United States Patent [19]
Yoshihama et al.

[11] Patent Number: 6,143,779
[45] Date of Patent: Nov. 7, 2000

[54] BENZOFURANONE DERIVATIVES AND A METHOD FOR PRODUCING THEM

[75] Inventors: Makoto Yoshihama; Masamichi Nakakoshi; Junji Nakamura; Shoji Nakayama, all of Tochigi, Japan

[73] Assignee: Snow Brand Milk Products Co., Ltd., Hokkaido, Japan

[21] Appl. No.: 09/142,666

[22] PCT Filed: Jan. 13, 1998

[86] PCT No.: PCT/JP98/00090

§ 371 Date: Dec. 7, 1998

§ 102(e) Date: Dec. 7, 1998

[87] PCT Pub. No.: WO98/30556

PCT Pub. Date: Jul. 16, 1998

[30] Foreign Application Priority Data

Jan. 14, 1997 [JP] Japan ................................. 9-015991
Aug. 8, 1997 [JP] Japan ................................. 9-225565

[51] Int. Cl.[7] .................................................. A61K 31/34
[52] U.S. Cl. ........................ 514/470; 549/304; 549/310; 549/466
[58] Field of Search ........................... 514/470; 549/304, 549/310, 466

[56] References Cited

U.S. PATENT DOCUMENTS 3,975,380  8/1976  Snader et al. ...................... 260/240 R

*Primary Examiner*—Amelia Owens
*Attorney, Agent, or Firm*—Townsend and Townsend and Crew LLP

[57] ABSTRACT

The present invention provides new benzofuranone derivatives and a method for producing the derivatives useful for a therapeutic agent for preventing and/or treating hormone dependent diseases.

The present invention is a new benzofuranone derivative represented by a particular general formula (I).

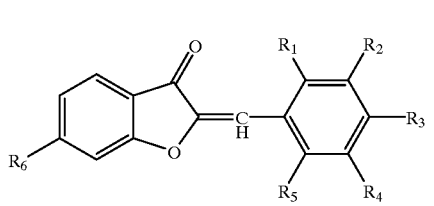

In the production, a particular benzofuranone compound and a particular benzaldehyde are reacted.

10 Claims, 8 Drawing Sheets

Fig. 1

| Example | structural formula | molecular formula | molecular weight | 17β-HSD inhibition activity (%) *1 | E2 in blood (pg/ml) *2 4hrs. | E2 in blood (pg/ml) *2 24hrs. |
|---|---|---|---|---|---|---|
| 1 | HO-[benzofuranone]-CH=C6H4-OH | $C_{15}H_{10}O_4$ | 254.244 | 70.0±2.3 | 8.3 ±1.6 | 40.4±9.2 |
| 2 | HO-[benzofuranone]-CH=C6H3(Cl)(NH2) | $C_{15}H_{10}ClNO_3$ | 287.704 | 7.2±2.1 | — | — |
| 3 | HO-[benzofuranone]-CH2-C6H3(Cl)(NH2) | $C_{15}H_{10}ClNO_3$ | 287.704 | 20.3±1.8 | — | — |
| 4 | HO-[benzofuranone]-CH=C6H3(OCH3)(OCH3) | $C_{17}H_{14}O_5$ | 298.297 | 1.6±1.1 | — | — |
| 5 | HO-[benzofuranone]-CH2-C6H3(OCH3)(OCH3) | $C_{17}H_{14}O_5$ | 298.297 | 68.2±5.7 | 12.3 ±2.4 | 33.0±16.7 |
| 6 | HO-[benzofuranone]-CH=C6H3(OCH3)(OCH3) | $C_{17}H_{14}O_5$ | 298.297 | 45.7±9.4 | — | — |
| 7 | HO-[benzofuranone]-CH2-[benzodioxole] | $C_{17}H_{12}O_5$ | 296.281 | 54.7±3.8 | 7.8 ±3.3 | 15.1±2.3 |
| 8 | HO-[benzofuranone]-CH=[indole] | $C_{17}H_{11}NO_3$ | 277.281 | 37.9±2.1 | — | — |
| 9 | HO-[benzofuranone]-CH2-C6H4-iPr | $C_{18}H_{16}O_3$ | 280.325 | 27.6±3.3 | — | — |
| 10 | HO-[benzofuranone]-CH=C6H4-OCH3 | $C_{16}H_{12}O_4$ | 268.27 | 71.4±7.7 | 24.0 ±3.1 | 49.3±17.3 |

*1, *2; mean ± standard deviation

Fig. 2
| Example | structural formula | molecular formula | molecular weight | 17β-HSD inhibition activity (%) *1 | E2 in blood (pg/ml)*2 | |
|---|---|---|---|---|---|---|
| | | | | | 4hrs. | 24hrs. |
| 11 | 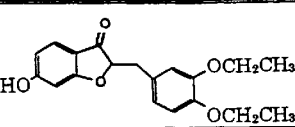 | $C_{19}H_{18}O_5$ | 326.351 | 39.6±4.5 | — | — |
| 12 | 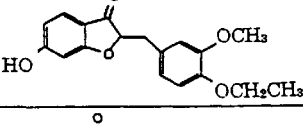 | $C_{18}H_{16}O_5$ | 312.324 | 58.9±2.2 | 0.9±1.7 | 15.7±2.1 |
| 13 | 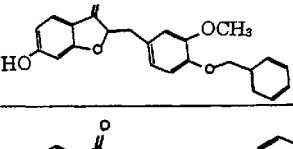 | $C_{23}H_{18}O_5$ | 374.395 | 36.2±3.2 | — | — |
| 14 | 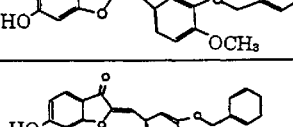 | $C_{23}H_{18}O_5$ | 374.395 | 49.5±5.5 | 5.0±3.7 | 15.9±3.7 |
| 15 | 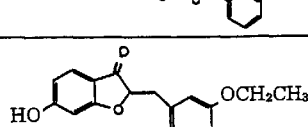 | $C_{29}H_{22}O_5$ | 450.494 | 23.2±4.2 | — | — |
| 16 | 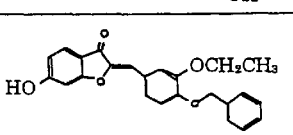 | $C_{17}H_{14}O_5$ | 298.297 | 46.9±4.4 | 8.7±2.7 | 23.0±1.2 |
| 17 | 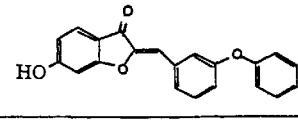 | $C_{24}H_{20}O_5$ | 388.422 | 37.0±3.3 | — | — |
| 18 | 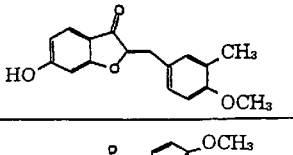 | $C_{21}H_{14}O_4$ | 330.342 | 35.3±7.1 | — | — |
| 19 | 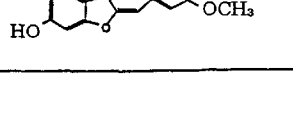 | $C_{17}H_{14}O_4$ | 282.297 | 52.6±4.4 | — | — |
| 20 |  | $C_{17}H_{14}O_5$ | 298.297 | 44.6±8.2 | 25.2±2.2 | 40.5±5.4 |
*1, *2; mean ± standard deviation

Fig. 3

| Example | structural formula | molecular formula | molecular weight | 17β-HSD inhibition activity (%) [1] | E2 in blood (pg/ml) [2] | |
|---|---|---|---|---|---|---|
| | | | | | 4hrs. | 24hrs. |
| 21 | HO-[benzofuranone]-CH$_2$-Ar(OCH$_2$CH$_3$, OCH$_3$) | $C_{18}H_{16}O_5$ | 312.324 | 55.7±6.9 | — | — |
| 22 | HO-[benzofuranone]-CH$_2$-Ar(CH$_3$, CH$_3$) | $C_{17}H_{14}O_3$ | 266.298 | 26.3±3.9 | — | — |
| 23 | HO-[benzofuranone]-CH$_2$-Ar(CH$_3$, OH) | $C_{16}H_{12}O_4$ | 268.270 | 77.1±9.7 | — | — |
| 24 | H$_3$COCO-[benzofuranone]=CH-Ar(OCH$_2$CH$_2$O) | $C_{19}H_{14}O_6$ | 338.318 | 74.9±4.2 | — | — |
| 25 | H$_3$COCO-[benzofuranone]=CH-Ar(OCH$_2$O) | $C_{18}H_{12}O_6$ | 324.291 | 67.9±5.2 | 4.3±5.2 | 20.3±3.3 |
| 26 | H$_3$COCO-[benzofuranone]-CH$_2$-Ar(OCH$_3$) | $C_{18}H_{14}O_5$ | 310.308 | 69.2±3.5 | — | — |
| 27 | H$_3$COCO-[benzofuranone]-CH$_2$-Ar(OCH$_3$, OCH$_3$) | $C_{19}H_{16}O_6$ | 340.334 | 68.4±3.7 | 11.7±1.5 | 41.8±17.5 |
| 28 | H$_3$COCO-[benzofuranone]-CH$_2$-Ar(OCH$_3$, OCH$_3$) | $C_{19}H_{16}O_6$ | 340.334 | 71.6±3.2 | 7.3±3.7 | 19.5±3.0 |
| 29 | H$_3$COCO-[benzofuranone]-CH$_2$-Ar(CH$_3$, OCH$_3$) | $C_{19}H_{16}O_5$ | 324.335 | 54.3±1.8 | — | — |
| 30 | PhCOO-[benzofuranone]-CH$_2$-Ar(OCH$_3$, OCH$_3$) | $C_{24}H_{18}O_6$ | 402.406 | 20.7±2.9 | 17.8±2.0 | 21.5±2.0 |

[1], [2]; mean ± standard deviation

Fig. 4

| Example | structural formula | molecular formula | molecular weight | 17β-HSD inhibition activity (%) *1 | E2 in blood (pg/ml)*2 | |
|---|---|---|---|---|---|---|
| | | | | | 4hrs. | 24hrs. |
| 31 | | $C_{24}H_{18}O_6$ | 402.406 | 19.8±2.3 | — | — |
| 32 | | $C_{23}H_{14}O_6$ | 386.363 | 5.7±2.1 | — | — |
| 33 | | $C_{24}H_{16}O_6$ | 400.390 | 8.8±3.0 | — | — |
| 34 | | $C_{24}H_{18}O_5$ | 386.406 | 11.0±2.7 | — | — |
| 35 | | $C_{23}H_{16}O_5$ | 372.379 | 16.3±2.1 | — | — |
| 36 | | $C_{23}H_{16}O_5$ | 372.379 | 8.9±2.0 | — | — |
| 37 | | $C_{19}H_{16}O_5$ | 324.335 | 71.9±3.4 | — | — |
| 38 | | $C_{19}H_{16}O_5$ | 324.335 | 69.3±9.2 | — | — |
| 39 | | $C_{20}H_{18}O_5$ | 338.362 | 77.0±6.2 | — | — |
| 40 | | $C_{20}H_{18}O_6$ | 354.361 | 73.5±2.8 | — | — |

*1, *2; mean ± standard deviation

Fig. 5

| Example | structural formula | molecular formula | molecular weight | 17β-HSD inhibition activity (%) *1 | E2 in blood (pg/ml)*2 4hrs. | E2 in blood (pg/ml)*2 24hrs. |
|---|---|---|---|---|---|---|
| 41 | (structure) | $C_{20}H_{18}O_6$ | 354.361 | 67.2±3.0 | 5.3±3.5 | 13.5±2.6 |
| 42 | (structure) | $C_{19}H_{16}O_6$ | 338.318 | 78.1±7.3 | 7.2±5.8 | 13.8±3.3 |
| 43 | (structure) | $C_{20}H_{16}O_6$ | 352.345 | 74.5±1.1 | — | — |
| 44 | (structure) | $C_{19}H_{18}O_4$ | 310.351 | 8.8±8.9 | — | — |
| 45 | (structure) | $C_{19}H_{18}O_4$ | 310.351 | 7.5±3.1 | — | — |
| 46 | (structure) | $C_{20}H_{20}O_5$ | 340.378 | 12.75±4.7 | — | — |
| 47 | (structure) | $C_{20}H_{20}O_5$ | 340.378 | 17.7±5.0 | — | — |
| 48 | (structure) | $C_{20}H_{20}O_4$ | 324.378 | 9.4±1.6 | — | — |
| 49 | (structure) | $C_{20}H_{18}O_5$ | 338.362 | 12.1±4.3 | — | — |
| 50 | (structure) | $C_{19}H_{16}O_5$ | 324.335 | 7.1±8.9 | — | — |

*1, *2: mean ± standard deviation

Fig. 6

| Example | structural formula | molecular formula | molecular weight | 17β-HSD inhibition activity (%) *1 | E2 in blood (pg/ml)*2 4hrs. | E2 in blood (pg/ml)*2 24hrs. |
|---|---|---|---|---|---|---|
| 51 | H3CO-[benzofuranone]-CH2-[phenyl(CH3)(OCH3)] | $C_{18}H_{16}O_4$ | 296.324 | 61.5±2.2 | — | — |
| 52 | H3CO-[benzofuranone]-CH2-[benzodioxole] | $C_{18}H_{14}O_5$ | 310.308 | 59.9±2.6 | 101.0±24.7*3 | 133.3±30.2*4 |
| 53 | H3CO-[benzofuranone]=CH-[phenyl-OCH3] | $C_{17}H_{14}O_4$ | 282.297 | 48.2±4.0 | — | — |
| 54 | HO-[benzofuranone]-CH2-[phenyl(OCH3)(OCH3)] | $C_{17}H_{14}O_4$ | 298.297 | 42.6±4.1 | — | — |
| 55 | HO-[benzofuranone]=CH-[phenyl(OCH3)(OCH2CH2CH3)] | $C_{19}H_{18}O_5$ | 326.351 | 47.4± | — | — |
| 56 | HO-[benzofuranone]-CH2-[phenyl(OCH3)(O(CH2)3CH3)] | $C_{20}H_{20}O_5$ | 340.378 | 41.2± | — | — |
| 57 | HO-[benzofuranone]=CH-[phenyl(OCH3)(O(CH2)4CH3)] | $C_{21}H_{22}O_5$ | 354.405 | 37.4± | — | — |
| 58 | HO-[benzofuranone]=CH-[phenyl(OCH3)(O(CH2)5CH3)] | $C_{22}H_{24}O_5$ | 368.432 | 31.5± | — | — |
| 59 | H3CH2CO-[benzofuranone]=CH-[benzodioxole] | $C_{19}H_{16}O_5$ | 324.335 | 5.5± | — | — |
| 60 | H3C(H2C)2O-[benzofuranone]=CH-[benzodioxole] | $C_{20}H_{18}O_5$ | 338.362 | 1.1± | — | — |

*1, *2; mean ± standard deviation    *3; dose 1mg/kg    *4; dose 10mg/kg

Fig. 7

| Example | structural formula | molecular formula | molecular weight | 17β-HSD inhibition activity (%) *1 | E2 in blood (pg/ml)*2 | |
|---|---|---|---|---|---|---|
| | | | | | 4hrs. | 24hrs. |
| 6 1 | H₃C(H₂C)₃O–[structure] | $C_{21}H_{20}O_5$ | 352.389 | 0.0± | — | — |
| 6 2 | H₃C(H₂C)₄O–[structure] | $C_{22}H_{22}O_5$ | 366.416 | 0.6± | — | — |
| 6 3 | H₃CH₂CO–[structure] | $C_{18}H_{14}O_5$ | 310.308 | 2.4± | — | — |
| 6 4 | H₃C(H₂C)₂O–[structure] | $C_{19}H_{16}O_5$ | 324.335 | 1.4± | — | — |
| 6 5 | H₃C(H₂C)₃O–[structure] | $C_{20}H_{18}O_5$ | 338.362 | 0.0± | — | — |
| 6 6 | H₃C(H₂C)₄O–[structure] | $C_{21}H_{20}O_5$ | 352.389 | 1.1± | — | — |
| 6 7 | H₃C(H₂C)₅O–[structure] | $C_{23}H_{24}O_5$ | 380.443 | 0.0± | — | — |
| 6 8 | H₃C(H₂C)₅O–[structure] | $C_{22}H_{22}O_5$ | 366.416 | 1.2± | — | — |
| 6 9 | H₃COOC–CH(CH₃)–[structure] | $C_{21}H_{18}O_7$ | 382.372 | 0.0± | — | — |
| 7 0 | HOOC–CH(CH₃)–[structure] | $C_{20}H_{16}O_7$ | 368.345 | 1.7± | — | — |

*1, *2; mean ± standard deviation

Fig. 8
| Example | structural formula | molecular formula | molecular weight | 17β-HSD inhibition activity (%) *1 | E2 in blood (pg/ml)*2 4hrs. | 24hrs. |
|---|---|---|---|---|---|---|
| 71 | 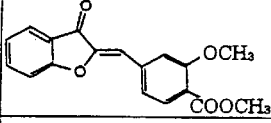 | $C_{18}H_{14}O_5$ | 310.308 | 51.7± | — | — |
| 72 | 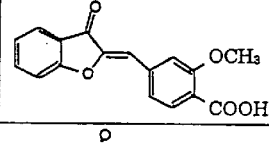 | $C_{17}H_{12}O_5$ | 296.281 | 56.4± | — | — |
| 73 | 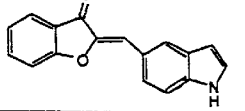 | $C_{17}H_{11}NO_2$ | 261.282 | 3.3± | — | — |
*1, *2; mean ± standard deviation

BENZOFURANONE DERIVATIVES AND A METHOD FOR PRODUCING THEM

TECHNICAL FIELD

The present invention relates to new benzofuranone derivatives and a method for producing the derivatives. The derivatives of the present invention have inhibition activity of 17β-hydroxysteroid dehydrogenase (abbreviated as 17β-HSD, hereinafter), and these derivatives are useful for a therapeutic agent for preventing and/or treating androgen or estrogen dependent diseases, particularly, prostatic cancer, benign prostatic hyperplasia, virilism, mammary cancer, mastopathy, endometrial cancer, endometriosis, ovarian cancer and the like.

BACKGROUND ART

Lately, in our country, it causes trouble that androgen dependent diseases such as prostatic cancer and benign prostatic hyperplasia, and estrogen dependent diseases such as mammary cancer and endometriosis, are increasing in the morbidity. For example, the percentage of mortality of the prostatic cancer was 3.9 men per 100,000 of population by statistical data in 1984, and was about $\frac{1}{10}$ of the non Caucasian men in the Western country. However, it is increasing gradually by prolonging life due to improvement of medical treatment and western diet. In 1993, that percentage is 6.7 men per 100,000 of population and it is coming to European and U.S. levels. It is expected that the numbers of mortality based on the prostatic cancer in 2015 will be four times more of those in 1990. This is the worst increasing percentage in all cancers.

It has become clear from many views that subjective conditions and objective conditions of the androgen dependent diseases will be improved by depressing the androgen levels in blood. Therefore, treatment of these diseases have been accomplished by lowering the androgen in blood by castration, by administering an agonist of the LH-RH to lower the androgen in blood to the castration level, and by administering anti-androgen agents antagonizing an androgen receptor to control the action of the androgen. In fact, the clinical effects are broadly noticed. However, since the castration causes a lowering of QOL, it is only proceeded in very limited diseases. The agonist of LH-RH has problems; side effect such as a bone pain or dysuria caused by a phenomenon peculiar to the agonist (temporary increase of the androgen), and rekindling for continuous existence of androgen originated from adrenal glands. Further, it is indicated that the effect of the anti-androgen agents is decreased by the development of variants of the androgen receptor during the medicine is administered. Therefore, "a method of complete blockage of the androgen" is prescribed for more effective endocrine therapeutics. The method is aimed to completely inhibit the androgen in blood by combination of several endocrine treatment methods, and more effective treatment is expected.

Testosterone exhibiting the most effective androgen activity in C19 steroids having androgenic activity can be synthesized with 17β-HSD from a substrate of andorostendione. By inhibiting this 17β-HSD, the concentration of testosterone in blood is directly lowered, so that it is expected to effectively treat the above androgen dependent diseases. In addition, since this enzyme is also a biosynthetic enzyme of estoradiol having the highest estrogen activity in $C_{18}$ steroid having estrogenic activity, it is also expected to effectively treat the estrogen dependent diseases such as mammary cancer and endometriosis.

Steroid compounds and non-steroid compounds have been proposed as 17β-HSD inhibitors. As the non-steroid compounds, for example, flavons and isoflavons, which are described in Biochemical and Biophysical Research Communications, Vol. 215, 1137–1144 (1995), and fatty acids, which are described in Journal of Steroid Biochemistry, Vol. 23, 357–363 (1985), are known. However, since the activity of these compounds is not satisfied, it is expected to obtain materials having higher activity.

DISCLOSURE OF INVENTION

Considering the above problems, the inventors of the present invention earnestly have studied and found that new benzofuranone derivatives have an excellent inhibition activity of 17β-HSD. Therefore, the present invention aims to provide the new benzofuranone derivatives and a method for producing the derivatives.

The present invention relates to new benzofuranone derivatives and a method for producing the derivatives. The derivatives of the present invention have inhibition activity of 17β-hydroxysteroid dehydrogenase (abbreviated as 17β-HSD, hereinafter), and these derivatives are useful for a therapeutic agent for preventing and/or treating androgen or estrogen dependent diseases, particularly, prostatic cancer, benign prostatic hyperplasia, virilism, mammary cancer, mastopathy, endometrial cancer, endometriosis, ovarian cancer and the like.

The derivatives of the present invention is a new benzofuranone derivative represented by the following general formula (I):

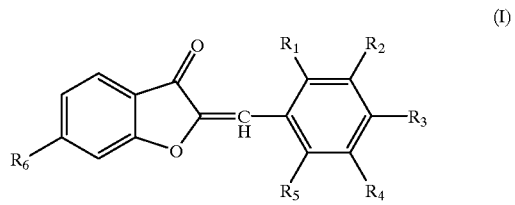

wherein $R_1$–$R_5$ represent hydrogen, a hydroxy group, or a straight or branched alkyl, alkyloxy or aralkyloxy group having 1–7 carbon atoms, a halogen, an amino group or an alkylene dioxy group joined at $R_1$ and $R_2$, $R_2$ and $R_3$, $R_3$ and $R_4$, or $R_4$ and $R_5$, respectively, $R_6$ represents a hydroxy group, or a straight or branched alkyloxy or aralkyloxy group having 1–7 carbon atoms, or a carboxylic acid ester having 1–7 carbon atoms.

In addition, the present invention is characterized in that, for producing the new benzofuranone derivative, a benzofuranone compound represented by the following general formula (II) and a benzaldehyde compound represented by the following general formula (III) are dissolved in an organic solvent and refluxed with heating or reacted at room temperature under acidic or basic conditions, and the desired compound is purified from the reactant.

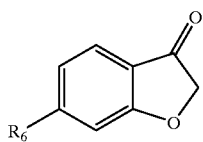

(II)

wherein R₆ represents a hydroxy group, a straight or branched alkyloxy or aralkyloxy group having 1–7 carbon atoms, or a carboxylic acid ester having 1–7 carbon atoms.

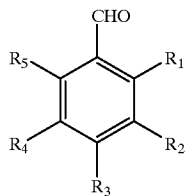

(III)

wherein $R_1$–$R_5$ represent hydrogen, a hydroxy group, or a straight or branched alkyl, alkyloxy or aralkyloxy group having 1–7 carbon atoms, a halogen, or an amino group, respectively.

As embodiments of new benzofuranone derivatives which are derivatives of the present invention and are represented by the general formula (I), the following compounds can be exemplified(the numbers of compounds and examples described in FIGS. 1–6 are coincident).

(1) 2-[(3-hydroxyphenyl)methylene]-6-hydroxy-3(2H)-benzofuranone
(2) 2-[(3-chloro-6-aminophenyl)methylene]-6-hydroxy-3(2H)-benzofuranone
(3) 2-[(4-chloro-3-aminophenyl)methylene]-6-hydroxy-3(2H)-benzofuranone
(4) 2-[(4,6-dimethoxyphenyl)methylene]-6-hydroxy-3(2H)-benzofuranone
(5) 2-[(3,5-dimethoxyphenyl)methylene]-6-hydroxy-3(2H)-benzofuranone
(6) 2-[(2,5-dimethoxyphenyl)methylene]-6-hydroxy-3(2H)-benzofuranone
(7) 2-[(1,4-benzodioxane)-6-methylene]-6-hydroxy-3(2H)-benzofuranone
(8) 2-[(indol)-3-methylene]-6-hydroxy-3(2H)-benzofuranone
(9) 2-[(4-isopropylphenyl)methylene]-6-hydroxy-3(2H)-benzofuranone
(10) 2-[(3-methoxyphenyl)methylene]-6-hydroxy-3(2H)-benzofuranone
(11) 2-[(3,4-diethoxyphenyl)methylene]-6-hydroxy-3(2H)-benzofuranone
(12) 2-[(3-methoxy-4-ethoxyphenyl)methylene]-6-hydroxy-3(2H)-benzofuranone
(13) 2-[(3-methoxy-4-benzyloxyphenyl)methylene]-6-hydroxy-3(2H)-benzofuranone
(14) 2-[(4-methoxy-3-benzyloxyphenyl)methylene]-6-hydroxy-3(2H)-benzofuranone
(15) 2-[(3,4-dibenzyloxyphenyl)methylene]-6-hydroxy-3(2H)-benzofuranone
(16) 2-[(3-ethoxy-4-hydroxyphenyl)methylene]-6-hydroxy-3(2H)-benzofuranone
(17) 2-[(3-ethoxy-4-benzyloxyphenyl)methylene]-6-hydroxy-3(2H)-benzofuranone
(18) 2-[(3-phenoxyphenyl)methylene]-6-hydroxy-3(2H)-benzofuranone
(19) 2-[(3-methyl-4-methoxyphenyl)methylene]-6-hydroxy-3(2H)-benzofuranone
(20) [E]-2-[(3,4-dimethoxyphenyl)methylene]-6-hydroxy-3(2H)-benzofuranone
(21) 2-[(3-ethoxy-4-methoxyphenyl)methylene]-6-hydroxy-3(2H)-benzofuranone
(22) 2-[(3,4-dimethylphenyl)methylene]-6-hydroxy-3(2H)-benzofuranone
(23) 2-[(3-methyl-4-hydoxyphenyl)methylene]-6-hydroxy-3(2H)-benzofuranone
(24) 2-[(1,4-bezodioxane)-6-methylene]-6-acetoxy-3(2H)-benzofuranone
(25) 6-acetoxy-2-piperonylidene-3(2H)-benzofuranone
(26) 2-[(3-methoxyphenyl)methylene]-6-acetoxy-3(2H)-benzofuranone
(27) 2-[(3,4-dimethoxyphenyl)methylene]-6-acetoxy-3(2H)-benzofuranone
(28) 2-[(3,5-dimethoxyphenyl)methylene]-6-acetoxy-3(2H)-benzofuranone
(29) 2-[(3-methyl-4-methoxyphenyl)methylene]-6-acetoxy-3(2H)-benzofuranone
(30) 2-[(3,4-dimethoxyphenyl)methylene]-6-benzoyloxy-3(2H)-benzofuranone
(31) 2-[(3,5-dimethoxyphenyl)methylene]-6-benzoyloxy-3(2H)-benzofuranone
(32) 6-benzoyloxy-2-piperonylidene-3(2H)-benzofuranone
(33) 2-[(1,4-benzodioxane)-6-methylene]-6-benzoyloxy-3(2H)-benzofuranone
(34) 2-[(3-methyl-4-methoxyphenyl)methylene]-6-benzoyloxy-3(2H)-benzofuranone
(35) 2-[(3-methoxyphenyl)methylene]-6-benzoyloxy-3(2H)-benzofuranone
(36) 2-[(4-methoxyphenyl)methylene]-6-benzoyloxy-3(2H)-benzofuranone
(37) 2-[(4-methoxyphenyl)methylene]-6-propionyloxy-3(2H)-benzofuranone
(38) 2-[(3-methoxyphenyl)methylene]-6-propionyloxy-3(2H)-benzofuranone
(39) 2-[(3-methyl-4-methoxyphenyl)methylene]-6-propionyloxy-3(2H )-benzofuranone
(40) 2-[(3,5-dimethoxyphenyl)methylene]-6-propionyloxy-3(2H)-benzofuranone
(41) 2-[(3,4-methoxyphenyl)methylene]-6-propionyloxy-3(2H)-benzofuranone
(42) 6-propionyloxy-2-piperonylidene-3(2H)-benzofuranone
(43) 2-[(1,4-benzodioxane) -6-methylene]-6-propionyloxy-3(2H)-benzofuranone
(44) 2-[(4-methoxyphenyl)methylene]-6-isopropyloxy-3(2H)-benzofuranone
(45) 2-[(3-methoxyphenyl)methylene]-6-isopropyloxy-3(2H)-benzofuranone
(46) 2-[(3,4-dimethoxyphenyl)methylene]-6-isopropyloxy-3(2H)-benzofuranone
(47) 2-[(3,5-dimethoxyphenyl)methylene]-6-isopropyloxy-3(2H)-benzofuranone
(48) 2-[(3-methyl-4-methoxyphenyl)methylene]-6-isopropyloxy -3(2H)-benzofuranone
(49) 2-[(1,4-benzodioxane)-6-methylene]-6-isopropyloxy-3(2H)-benzofuranone
(50) 6-isopropyloxy-2-piperonylidene-3(2H)-benzofuranone (51) 2-[(3-methyl-4-methoxyphenyl)methylene]-6-methoxy-3(2H)-benzofuranone
(52) 2-[(1,4-benzodioxane)-6-methylene]-6-methoxy-3(2H)-benzofuranone
(53) 2-[(3-methoxyphenyl)methylene]-6-methoxy-3(2H)-benzofuranone

(54) 2-[(2,4-dimethoxyphenyl)methylene]-6-hydroxy-3 (2H)-benzofuranone
(55) 2-[(3-methoxy-4-propyloxyphenyl)methylene]-6-hydroxy-3(2H)- benzofuranone
(56) 2-[(3-methoxy-4-butoxyphenyl)methylene]-6-hydroxy-3(2H)-benzofuranone
(57) 2-[(3-methoxy-4-pentyloxyphenyl)methylene]-6-hydroxy-3(2H)-benzofuranone
(58) 2-[(3-methoxy-4-hexyloxyphenyl)methylene]-6-hydroxy-3(2H)-benzofuranone
(59) 2-[(1,4-benzodioxane)-6-methylene]-6-ethoxy-3(2H)-benzofuranone
(60) 2-[(1,4-benzodioxane)-6-methylene]-6-propyloxy-3(2H)-benzofuranone
(61) 2-[(1,4-benzodioxane)-6-methylene]-6-butoxy-3(2H)-benzofuranone
(62) 2-[(1,4-benzodioxane)-6-methylene]-6-pentyloxy-3(2H)-benzofuranone
(63) 6-ethoxy-2-piperonylidene-3(2H)-benzofuranone
(64) 6-propyloxy-2-piperonylidene-3(2H)-benzofuranone
(65) 6-butoxy-2-piperonylidene-3(2H)-benzofuranone
(66) 6-pentyloxy-2-piperonylidene-3(2H)-benzofuranone
(67) 2-[(1,4-benzodioxane)-6-methylene]-6-hexyloxy-3 (2H)-benzofuranone
(68) 6-hexyloxy-2-piperonylidene-3(2H)-benzofuranone
(69) methyl-2-({2-[1-(2,3-dihydro-1,4-benzodioxine-6-yl) methylidene]-3-oxo-2,3 -dihydrobenzo[b]furan-6-yl}oxy)propionate
(70) 2-({2-[1-(2,3-dihydro-1,4-benzodioxine-6-yl) methylidene]-3-oxo-2,3-dihydrobenzo[b]furan-6-yl}oxy) propionic acid
(71) methyl-2-methoxy-4-[(3-oxo-2,3-dihydrobenzo[b] furan-2-ylidene)methyl]benzoate
(72) 2-methoxy-4-[(3-oxo-2,3-dihydrobenzo[b]furan-2-ylidene)methyl]benzoate
(73) 2-[1-(1H-5-indolyl)methylidene]-2,3-dihydrobenzo[b]furan-3-one The derivatives of the present invention contain, in addition to the above-mentioned compounds, stereospecific isomers of these compounds, and salts formed with acids or bases. As the salts of bases, for example, salts of inorganic bases of sodium, potassium, magnesium, calcium or aluminum, salts of organic bases of lower alkyl amines or lower alcohol amines, salts of basic amino acids such as lysine, alginine, or ornithine, or ammonium salts are exemplified. Further, the derivatives may form hydrates, solvates of lower alcohols, and crystal polymorphs.

The derivatives of the present invention can be prepared by the following methods. As an example, above-mentioned benzofuranone compounds (II) and above-mentioned benzaldehyde compounds (III) are dissolved in solvent such as methanol, ethanol or propanol, concentrated hydrochloric acid is added, the solution is refluxed with heating for 1–24 hours and cooled, precipitated crystals are filtered to obtain desired new benzofuranone derivative (I) which is a derivative of the present invention. When crystals are not precipitated, water 100–400 ml is added to precipitate crystals, and the crystals are filtered and dried to obtain the desired derivative of the present invention. Otherwise, sodium hydroxide or potassium hydroxide is added to compounds (II) and (III) in solvent such as methanol, ethanol or propanol, the solution is stirred for 1–24 hours and acidified with hydrochloric acid, and precipitated crystals are filtered to obtain the desired derivative of the present invention. In addition, the desired derivatives of the present invention can be obtained by dissolving the above compounds in a hydrochloric gas-saturated solution of organic solvent such as methanol, ethanol, propanol or ether; then cooling, allowing to stand at room temperature or heating the solution; stirring for 1–24 hours; adding water to precipitate the desired derivatives as crystals; and filtering the precipitated crystals.

When the derivatives of the present invention can safely be orally or parenterally administered as medicines to man or animals. In the case of parenteral administration, intravenous injection, intramuscular injection, subcutaneous injection, intra-abdominal injection, percutaneous administration, administration through the lungs, intranasal injection, administration through the intestines, administration from oral cavity, and administration through mucosae can be exemplified, and these medicines are administered. Injections, suppository, aerosols and percutaneous absorption tapes and the like can be exemplified. As the medicines of oral administration, tablets (including sugar-coated tablets, coating tablets and buccal tablets), powder, capsules (including a soft capsule), granules (including a coating granule), pills, troches, liquid preparations, or sustained release preparations of these medicines, which are pharmaceutically allowable, can be exemplified. As the liquid for oral administration, suspension, emulsion, syrup (including dry syrup), and elixir can be exemplified. These pharmaceuticals are prepared by conventional methods of manufacturing pharmacy and administered as drug compositions along with pharmacologically allowable carriers, vehicles, disintegrators, lubricants, coloring matters and the like.

As the carriers and vehicles used in these pharmaceuticals, lactose, glucose, sucrose, mannitol, potato starch, corn starch, calcium carbonate, calcium phosphate, calcium sulfate, crystalline cellulose, powdered glycyrrhiza, and powdered gentian can be exemplified. As the binders, starch, tragacanth gum, gelatin, syrup, polyvinylalcohol, polyvinylether, polyvinylpyrrolidone, hydroxypropylcellulose, methylcellulose, ethylcellulose, and carboxymethylcellulose can be exemplified. As the disintegrators, starch, agar, powdered gelatin, sodium carboxymethylcellulose, calcium carboxymethylcellulose, crystalline cellulose, calcium carbonate, calcium bicarbonate, and sodium alginic acid can be exemplified. As the lubricants, magnesium stearate, talc, hydrogenated vegetable oil, and macrogol can be exemplified. As the coloring matters, matters which are allowed to add to medicines can be used.

The tablets and granules can be coated with sucrose, gelatin, hydroxypropylcellulose, purified shellac, gelatin, glycerin, sorbitol, ethylcellulose, hydroxypropylcellulose, hydroxypropylmethylcellulose, polyvinylpyrrolidone, phthalic acid cellulose acetate, hydroxypropylmethylcellulose phthalate, methylmethacrylate, methacryic acid polymer or the like, and one or more coatings may be used. Capsules of ethylcellulose or gelatin may be used. Further, when the injections are prepared, if necessary, a pH adjustor, a buffering agent, a stabilizer, a solubilizing agent or the like may be added to the basis by a conventional method.

When the derivatives of the present invention are administered to patients, the dose is not particularly limited because conditions such as the condition of illness, and patient's age, health condition and weight are different, it is about 1 mg–1,000 mg per day for an adult, preferably 50–200 mg, orally or parenterally one time or more a day.

BRIEF DESCRIPTION OF THE DRAWINGS

[FIG. 1] A drawing, which shows the results of examples.
[FIG. 2] A drawing, which shows the results of examples.
[FIG. 3] A drawing, which shows the results of examples.
[FIG. 4] A drawing, which shows the results of examples.

[FIG. 5] A drawing, which shows the results of examples.
[FIG. 6] A drawing, which shows the results of examples.
[FIG. 7] A drawing, which shows the results of examples.
[FIG. 8] A drawing, which shows the results of examples.

BEST MODE FOR CARRYING OUT THE INVENTION

The following Examples are intended to further illustrate the present invention and not to limit the invention by these Examples.

EXAMPLE 1

Synthesis of 2-[(3-hydroxyphenyl)methylene]-6-hydroxy-3(2H)-benzofuranone

After 6-hydroxy-2H-benzofuran-3-one 1 g and 3-hydroxybenzaldehyde 0.813 g were dissolved in methanol 75 ml, concentrated hydrochloric acid 50 ml was added, and the mixture was refluxed for two hours. The solution was cooled to room temperature, water 400 ml was added and allowed to stand for one hour. Precipitated crystals were filtered. The crystals were dried over phosphorous pentoxide at a temperature of 60° C. for five hours under reduced pressure to obtain the desired compound 1.20 g.

FAB MASS; 255 (M+1)
$^1$H-NMR (ppm, in DMSO-$d_6$); 6.67 (1H, s), 6.71 (1H, dd, J=8.5, 1.8 Hz), 6.77 (1H, d, J=1.8 Hz), 6.83 (1H, ddd, J=8.0, 2.5, 0.9 Hz), 7.27 (1H, t, J=8.0 Hz), 7.26 (1H, d, J=9.4 Hz), 7.38 (1H, t, J=2.1, 2.1 Hz), 7.62 (1H, d, J=9.6 Hz), 9.64 (1H, s), 11.20 (1H, s)

EXAMPLE 2

Synthesis of 2-[(3-chloro-6-aminophenyl)methylene]-6-hydroxy-3(2H)-benzofuranone After 6-hydroxy-2H-benzofuran-3-one 1 g and 3-chloro-6-aminobenzaldehyde 1.24 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for five hours under reduced pressure to obtain the desired compound 1.42 g.

$^1$H-NMR (ppm, in DMSO-$d_6$); 7.05 (1H, dd, J=8.5, 2.1 Hz), 7.14 (1H, d, J=1.5 Hz), 7.80 (1H, d, J=8.8, 2.4 Hz), 8.21 (1H, d, J=2.5 Hz), 8.26 (1H, d, J=9.6 Hz), 8.31 (1H, d, J=8.8 Hz), 8.63 (1H, s)

EXAMPLE 3

Synthesis of 2-[(3-chloro-4-aminophenyl)methylene]-6-hydroxy-3(2H)-benzofuranone After 6-hydroxy-2H-benzofuran-3-one 1 g and 3-chloro-4-aminobenzaldehyde 1.24 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for five hours under reduced pressure to obtain the desired compound 1.75 g.

$^1$H-NMR (ppm, in DMSO-$d_6$); 7.05 (1H, d, J=8.5 Hz), 7.14 (1H, d, J=1.5 Hz), 7.64 (1H, dd, J=8.5, 1.8 Hz), 8.16 (1H, d, J=8.5 Hz), 8.26 (1H, s), 8.29 (1H, d, J=8.8 Hz), 8.70 (1H, s)

EXAMPLE 4

Synthesis of 2-[(4,6-dimethoxyphenyl)methylene]-6-hydroxy-3(2H)-benzofuranone

After 6-hydroxy-2H-benzofuran-3-one 1 g and 4,6-dimethoxybenzaldehyde 1.23 g were dissolved in methanol 75 ml, concentrated hydrochloric acid 50 ml was added, and the mixture was refluxed for 1.5 hours. The solution was cooled to room temperature, water 400 ml was added, and precipitated crystals were filtered and dried over phosphorous pentoxide at a temperature of 60° C. for four hours under reduced pressure to obtain the desired compound 0.95 g.

FAB MASS; 299 (M+1)
$^1$H-NMR (ppm, in DMSO-$d_6$); 3.83 (3H, s), 3.89 (3H, s), 6.33 (1H, d, J=2.4 Hz), 6.67 (1H, dd, J=8.8, 2.1 Hz), 6.21 (1H, dd, J=8.8, 2.1 Hz), 6.77 (1H, d, J=1.8 Hz), 7.01 (1H, s), 7.57 (1H, d, J=8.5 Hz), 8.09 (1H, d, J=8.8 Hz)

EXAMPLE 5

Synthesis of 2-[(3,5-dimethoxyphenyl)methylene]-6-hydroxy-3(2H)-benzofuranone

After 6-hydroxy-2H-benzofuran-3-one 1 g and 3,5-dimethoxybenzaldehyde 1.23 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.42 g.

FAB MASS; 299 (M+1)
$^1$H-NMR (ppm, in DMSO-$d_6$); 3.77 (6H, s), 6.55 (1H, m), 6.67 (1H, s), 6.71 (1H, dd, J=8.5, 2.1 Hz), 6.79 (1H, d, J=2.1 Hz), 7.09 (2H, d, J=2.1 Hz), 7.59 (1H, d, J=8.2 Hz)

EXAMPLE 6

Synthesis of 2-[(2,5-dimethoxyphenyl)methylene]-6-hydroxy-3(2H)-benzofuranone

After 6-hydroxy-2H-benzofuran-3-one 1 g and 2,5-dimethoxybenzaldehyde 1.23 g were dissolved in methanol 75 ml, concentrated hydrochloric acid 50 ml was added, and the mixture was refluxed for 1.5 hours. The solution was cooled to room temperature, water 400 ml was added and precipitated crystals were filtered and dried over phosphorous pentoxide at a temperature of 60° C. for four hours under reduced pressure to obtain the desired compound 1.21 g.

FAB MASS; 299 (M+1)
$^1$H-NMR (ppm, in DMSO-$d_6$); 3.76 (3H, s), 3.82 (3H, s), 6.71 (1H, dd, J=8.5, 1.8 Hz), 6.78 (1H, d, J=1.8 Hz), 6.99 (3H, m), 7.59 (1H, d, J=8.5 Hz), 7.66 (1H, d, J=2.7 Hz), 11.16 (1H, s)

EXAMPLE 7

Synthesis of 2-[(1.4-benzodioxane)-6-methylene]-6-hydroxy-3(2H)-benzofuranone

PRODUCTION EXAMPLE 1

After 6-hydroxy-2H-benzofuran-3-one 1 g and 1,4-benzodioxane-6-carboxyaldehyde 1.21 g were dissolved in methanol 75 ml, concentrated hydrochloric acid 55 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.17 g.

FAB MASS; 297 (M+1)
$^1$H-NMR (ppm, in DMSO-$d_6$); 4.28 (4H, m), 6.67 (1H, s), 6.70 (1H, dd, J=8.2, 1.8 Hz), 6.77 (1H, d, J=2.1 Hz), 6.64 (1H, d, J=8.2), 7.41 (1H, dd, J=8.5, 2.1 Hz), 7.47 (1H, d, J=2.1 Hz), 7.58 (1H, d, J=8.2 Hz), 11.96 (1H, s)

PRODUCTION EXAMPLE 2

After 6-hydroxy-2H-benzofuran-3-one 50 g and 1,4-benzodioxane-6-carboxyaldehyde 60 g were dissolved in acetic acid 1,000 ml, concentrated hydrochloric acid 55 ml was added, and the mixture was stirred for two hours. The precipitated crystals were filtered and dried over phosphorous pentoxide at a temperature of 60° C. for 18 hours to obtain the desired compound 97.6 g.

MASS and NMR of Production Example 2 are each coincide with these of Production Example 1.

EXAMPLE 8

Synthesis of 2-[(indol)-3-methylene]-6-hydroxy-3(2H)-benzofuranone

After 6-hydroxy-2H-benzofuran-3-one 1 g and indol-3-carboxyaldehyde 1.15 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 0.495 g.

FAB MASS; 278 (M+1)

$^1$H-NMR (ppm, in DMSO-$d_6$); 6.72 (1H, dd, J=8.5, 2.1 Hz), 6.87 (1H, d, J=2.1 Hz), 7.16 (1H, s), 7.19 (2H, m), 7.49 (1H, d, J=7.9 Hz), 7.58 (1H, d, J=8.5 Hz), 7.99 (1H, d, J=7.9 Hz), 8.17 (1H, d, J=2.7 Hz), 12.08 (1H, s)

EXAMPLE 9

Synthesis of 2-[(4-isopropylphenyl)methylene]-6-hydroxy-3(2H)-benzofuranone

After 6-hydroxy-2H-benzofuran-3-one 1 g and cinnamic aldehyde 1.09 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 0.66 g.

FAB MASS; 281 (M+1)

$^1$H-NMR (ppm, in DMSO-$d_6$); 1.20 (6H, d, J=8.7 Hz), 2.91 (1H, m), 6.71 (1H, dd, J=9.1, 1.8 Hz), 6.74 (1H, s), 6.78 (1H, d, J=2.1 Hz), 7.34 (2H, d, J=8.2 Hz), 7.60 (2H, d, 8.5 Hz), 7.84 (1H, d, J=8.2 Hz), 11.12 (1H, s)

EXAMPLE 10

Synthesis of 2-[(3-methoxyphenyl)methylene]-6-hydroxy-3 (2H)-benzofuranone

After 6-hydroxy-2H-benzofuran-3-one 1 g and 3-methoxybenzaldehyde 1.125 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.22 g.

FAB MASS; 269 (M+1)

$^1$H-NMR (ppm, in DMSO-$d_6$); 3.78 (3H, s), 6.70 (1H, dd, J=8.8, 2.1 Hz), 6.72 (1H, s), 6.78 (1H, d, J=2.2 Hz), 6.97 (1H, dd, J=8.2, 2.4 Hz), 7.36 (1H, t, J=7.9 Hz), 7.46 (1H, m), 7.51 (1H, d, J=7.6 Hz), 7.60 (1H, d, J=8.5 Hz), 11.18 (1H, s)

EXAMPLE 11

Synthesis of 2-[(3,4-diethoxyphenyl)methylene]-6-hydroxy-3(2H)-benzofuranone

After 6-hydroxy-2H-benzofuran-3-one 1 g and 3,4-diethoxybenzaldehyde 1.58 ml were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.27 g.

FAB MASS; 326 (M+1)

$^1$H-NMR (ppm, in DMSO-$d_6$); 1.33 (3H, t), 1.35 (3H, t), 4.06 (4H, m), 6.69 (1H, dd, J=8.5, 1.8 Hz), 6.72 (1H, s), 6.77 (1H, d, J=1.8 Hz), 7.01 (1H, d, J=8.8 Hz), 7.50 (2H, m), 7.57 (1H, d, J=8.2 Hz), 11.08 (1H, s)

EXAMPLE 12

Synthesis of 2-[(3-methoxy-4-ethoxyphenyl)methylene]-6-hydroxy-3(2H)-benzofuranone After 6-hydroxy-2H-benzofuran-3-one 1 g and 3-methoxy-4-ethoxybenzaldehyde 1.33 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.55 g.

FAB MASS; 313 (M+1)

$^1$H-NMR (ppm, in DMSO-$d_6$); 1.33 (3H, t), 3.82 (3H, s), 4.05 (2H, q), 6.70 (1H, dd, J=8.5, 1.8 Hz), 6.73 (1H, s), 6.78 (1H, d, J=1.8 Hz), 7.01 (1H, d, J=8.2 Hz), 7.50 (2H, m), 7.58 (1H, d, J=8.5 Hz), 11.09 (1H, s)

EXAMPLE 13

Synthesis of 2-[(3-methoxy-4-benzyloxyphenyl)methylene]-6-hydroxy-3(2H)-benzofuranone After 6-hydroxy-2H-benzofuran-3-one 1 g and 3-methoxy-4-benzyloxybenzaldehyde 1.79 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.63 g.

FAB MASS; 375 (M+1)

$^1$H-NMR (ppm, in DMSO-$d_6$); 3.84 (3H, s), 5.14 (2H, s), 6.70 (1H, dd, J=8.2, 1.8 Hz), 6.75 (1H, s), 6.79 (1H, d, J=1.8 Hz), 7.13 (1H, d, J=8.3 Hz), 7.33–7.60 (8H, m), 11. 11 (1H, s)

EXAMPLE 14

Synthesis of 2-[(4-methoxy-3-benzyloxyphenyl)methylene]-6-hydroxy-3(2H)-benzofuranone After 6-hydroxy-2H-benzofuran-3-one 1 g and 4-methoxy-3-benzyloxybenzaldehyde 1.79 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.69 g.

FAB MASS; 375 (M+1)

$^1$H-NMR (ppm, in DMSO-$d_6$); 3.83 (3H, s), 5.18 (2H, s), 6.70 (1H, ddd, J=8.2, 1.8, 0.6 Hz), 6.71 (1H, s), 6.80 (1H, d, J=1.5 Hz), 7.06 (1H, d, J=8.2 Hz), 7.33–7.64 (8H, m), 11.12 (1H, s)

EXAMPLE 15

Synthesis of 2-[(3,4-dibenzyloxyphenyl)methylene]-6-hydroxy-3(2H)-benzofuranone

After 6-hydroxy-2H-benzofuran-3-one 1 g and 3,4-dibenzyloxybenzaldehyde 2.35 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.82 g.

FAB MASS; 451 (M+1)

$^1$H-NMR (ppm, in DMSO-d$_6$); 5.20 (2H, s), 5.22 (2H, s), 6.70 (1H, s), 6.71 (1H, dd, J=8.5, 1.8, 0.6 Hz), 6.81 (1H, d, J=1.8 Hz), 7.14 (1H, d, J=8.5 Hz), 7.31–7.51 (11H, m), 7.59 (1H, d, J=8.5 Hz), 7.65 (1H, d, J=1.8 Hz), 11.15 (1H, s)

EXAMPLE 16

Synthesis of 2-[(3-ethoxy-4-hydroxyphenyl)methylene]-6-hydroxy-3(2H)-benzofuranone After 6-hydroxy-2H-benzofuran-3-one 1 g and 3-ethoxy-4-hydroxybenzaldehyde 1.22 g were dissolved in methanol 75 ml, concentrated -hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.19 g.

FAB MASS; 299 (M+1)

$^1$H-NMR (ppm, in DMSO-d$_6$); 1.35 (3H, t), 3.82 (3H, s), 4.07 (2H, q), 6.70 (1H, s), 6.72 (1H, dd, J=8.2, 1.8 Hz), 6.82 (1H, d, J=2.1 Hz), 6.91 (1H, d, J=8.2 Hz), 7.44 (1H, dd, J=8.2, 1.8 Hz), 7.49 (1H, d, J=1.9 Hz), 7.57 (1H, d, J=8.2 Hz)

EXAMPLE 17

Synthesis of 2-[(3-ethoxy-4-benzyloxyphenyl)methylene]-6-hydroxy-3(2H)-benzofuranone After 6-hydroxy-2H-benzofuran-3-one 1 g and 3-ethoxy-4-benzyloxybenzaldehyde 1.80 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.33 g.

FAB MASS; 389 (M+1)

1H-NMR (ppm, in DMSO-d$_6$); 1.34 (3H, t), 4.08 (3H, s), 5.14 (2H, s), 6.70–6.73 (3H, m), 6.79 (1H, s), 7.08 (1H, d, J=8.5 Hz), 7.39–7.60 (8H, m), 11.11 (1H, s)

EXAMPLE 18

Synthesis of 2-[(3-phenoxyphenyl)methylene]-6-hydroxy-3 (2H)-benzofuranone

After 6-hydroxy-2H-benzofuran-3-one 1 g and 3-phenoxybenzaldehyde 1.27 ml were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 1.10 g.

FAB MASS; 331 (M+1)

$^1$H-NMR (ppm, in DMSO-d$_6$); 6.67 (1H, d, J=1.8 Hz), 6.70 (1H, dd, J=8.5, 2.2 Hz), 6.76 (1H, s), 7.02–7.21 (3H, m), 7.41–7.67 (6H, m), 11.23 (1H, s)

EXAMPLE 19

Synthesis of 2-[(3-methyl-4-methoxyphenyl)methylene]-6-hydroxy-3(2H)-benzofuranone After 6-hydroxy-2H-benzofuran-3-one 1 g and 3-methyl-4-methoxybenzaldehyde 1.11 g were dissolved in methanol 75 ml, concentrated hydrochloric acid 50 ml was added, and the mixture was refluxed for 1.5 hours. The solution was cooled to room temperature, and precipitated crystals were filtered and dried over phosphorous pentoxide at a temperature of 60° C. for four hours under reduced pressure to obtain the desired compound 0.75 g.

FAB MASS; 283 (M+1)

$^1$H-NMR (ppm, in DMSO-d$_6$); 2.18 (3H, s), 3.83 (3H, s), 6.68 (1H, s), 6.70 (1H, dd, J=8.5, 2.6 Hz), 7.03 (1H, d, J=8.5 Hz), 7.58 (1H, d, J=8.2), 7.71 (1H, d, J=2.1 Hz), 7.78 (1H, dd, J=8.5, 1.8 Hz), 11.11 (1H, s)

EXAMPLE 20

Synthesis of [E]-2-[(3,4-dimethoxyphenyl)methylene]-6-hydroxy-3(2H)-benzofuranone After 6-hydroxy-2H-benzofuran-3-one 1 g and 3,4 dimethoxybenzaldehyde 1.23 g were dissolved in acetic acid 20 ml, concentrated hydrochloric acid 1.1 ml was added, and the mixture was stirred for 18 hours, and methanol 15 ml was added. Precipitated crystals were filtered and dried over phosphorous pentoxide at a temperature of 60° C. for four hours under reduced pressure to obtain the desired compound 0.82 g.

FAB MASS; 299 (M+1)

$^1$H-NMR (ppm, in DMSO-d$_6$); 3.81 (3H, s), 3.82 (3H, s), 6.70 (1H, dd, J=8.8, 1.8 Hz), 6.74 (1H, s), 6.78 (1H, d, J=8.8 Hz), 7.55 (2H, m), 7.59 (1H, d, J=8.5 Hz), 11.09 (1H, s)

EXAMPLE 21

Synthesis of 2-[(3-ethoxy-4-methoxyphenyl)methylene]-6-hydroxy-3(2H)-benzofuranone After 6-hydroxy-2H-benzofuran-3-one 1 g and 3-ethoxy-4-methoxybenzaldehyde 1.33 g were dissolved in methanol 75 ml, concentrated hydrochloric acid 50 ml was added, and the mixture was refluxed for 1.5 hours. The solution was cooled to room temperature, and water 150 ml was added. Precipitated crystals were filtered and dried over phosphorous pentoxide at a temperature of 60° C. for four hours under reduced pressure to obtain the desired compound 0.99 g.

FAB MASS; 313 (M+1)

$^1$H-NMR (ppm, in DMSO-d$_6$); 1.35 (3H, t, J=6.7 Hz), 3.80 (3H, s), 4.06 (2H, q, J=6.7 Hz), 6.71 (1H, d, J=2.1 Hz), 7.03 (1H, d, J=8.2 Hz), 7.51 (2H, m), 7.58 (1H, d, J=8.2 Hz)

EXAMPLE 22

Synthesis of 2-[(3,4-dimethylphenyl)methylene]-6-hydroxy-3(2H)-benzofuranone

After 6-hydroxy-2H-benzofuran-3-one 1 g and 3,4-dimethylbenzaldehyde 1.07 g were dissolved in methanol 75 ml, concentrated hydrochloric acid 50 ml was added, and the mixture was refluxed for two hours. The solution was cooled to room temperature, and water 200 ml was added. Precipitated crystals were filtered and dried over phosphorous pentoxide at a temperature of 60° C. for four hours under reduced pressure to obtain the desired compound 1.21 g.

FAB MASS; 267 (M+1)

$^1$H-NMR (ppm, in DMSO-d$_6$); 2.24 (3H, s), 2.25 (3H, s), 6.67 (1H, s), 6.71 (1H, dd, J=8.2, 1.8 Hz), 6.78 (1H, d, J=1.8 Hz), 7.22 (1H, d, J=7.9 Hz), 7.59 (1H, d, J=8.5 Hz), 7.66 (2H, m), 11.16 (1H, s)

EXAMPLE 23

Synthesis of 2-[(3-methyl-4-hydroxyphenyl)methylene]-6-hydroxy-3(2H)-benzofuranone After 6-hydroxy-2H-benzofuran-3-one 1 g and 3-methyl-4-hydroxybenzaldehyde 1.00 g were dissolved in methanol 70 ml, concentrated hydrochloric acid 60 ml was added, and the mixture was refluxed for 1.5 hours. The solution was cooled to room temperature, and water 250 ml was added. Precipitated crystals were filtered and dried over phosphorous pentoxide at a temperature of 60° C. for four hours under reduced pressure to obtain the desired compound 1.22 g.

FAB MASS; 268 (M+1)

$^1$H-NMR (ppm, in DMSO-$d_6$); 2.18 (3H, s), 6.65 (1H, s), 6.76 (1H, dd, J=8.5, 1.8 Hz), 6.76 (1H, d, J=1.8 Hz), 7.90 (1H, d, J=8.8 Hz), 7.57 (1H, d, J=8.5 Hz), 7.66 (2H, m)

EXAMPLE 24

Synthesis of 2-[(1,4-benzodioxane)methylene]-6-acetoxy-3(2H)-benzofuranone

After 2-[(1,4-benzodioxane)-6-methylene]-6-hydroxy-3(2H)-benzofuranone 0.5 g was dissolved in pyridine 5 ml, acetyl chloride 0.2 ml was added, and the mixture was refluxed for 1.5 hours. This reaction mixture was cooled to room temperature, 2N-hydrochloric acid 50 ml was added, and the desired compound fraction was extracted twice with ethyl acetate 50 ml. After the ethyl acetate solution was washed with a saturated aqueous solution of sodium bicarbonate, the ethyl acetate phase was dehydrated with anhydrous magnesium sulfate and concentrated under reduced pressure. The crude extract was fractionated by silica gel column chromatography (silica gel: 50 g, eluted with solvent 400 ml of hexane:ethyl acetate=1:1) and the fraction was concentrated to dryness at a temperature of 40° C. under reduced pressure. Ethyl acetate 2 ml and hexane 10 ml were added to the residue to precipitate crystals. The crystals were filtered and dried over phosphorous pentoxide at a temperature of 60° C. for four hours under reduced pressure to obtain the desired compound 355.2 mg.

FAB MASS; 339 (M+1)

$^1$H-NMR (ppm, in CDCl$_3$); 2.32 (3H, s), 4.27 (4H, m), 6.76 (1H, s), 6.88 (1H, d, J=8.2 Hz), 6.90 (1H, dd, J=8.5, 2.1 Hz), 7.11 (1H, d, J=1.8 Hz), 7.32 (1H, dd, J=8.2, 2.1 Hz), 7.47 (1H, d, J=2.1 Hz), 7.56 (1H, d, J=8.2 Hz)

EXAMPLE 25

Synthesis of 6-acetoxy-2-piperonylidene-3(2H)-benzofuranone

After 6-hydroxy-2-piperonylidene-3(2H)-benzofuranone 0.5 g was dissolved in pyridine 5 ml, acetyl chloride 0.2 ml was added, and the mixture was refluxed for two hours. The reaction mixture was cooled to room temperature, ethyl acetate 50 ml was added, and the mixture was washed with 2N-hydrochloric acid 50 ml twice. After the ethyl acetate solution was dehydrated with anhydrous magnesium sulfate, it was concentrated under reduced pressure. The crude extract was fractionated by silica gel column chromatography (silica gel: 50 g, eluted with solvent 500 ml of hexane-:ethyl acetate=1:1) and the fraction was concentrated to dryness at a temperature of 40° C. under reduced pressure to obtain crystals. The crystals were filtered and dried on phosphorous pentoxide at a temperature of 60° C. for four hours under reduced pressure to obtain the desired compound 539.5 mg.

FAB MASS; 383 (M+1)

$^1$H-NMR (ppm, in CDCl$_3$); 2.33 (3H, s), 6.02 (2H, s), 6.80 (1H, s), 6.85 (1H, d, J=8.2 Hz), 6.92 (1H, dd, J=8.2, 1.8 Hz), 7.13 (1H, d, J=1.8 Hz), 7.28 (1H, dd, J=8.2, 1.8 Hz), 7.52 (1H, d, J=1.5 Hz), 7.78 (1H, d, J=8.2 Hz)

EXAMPLE 26

Synthesis of 2-[(3-methoxyphenyl)methylene]-6-acetoxy-3(2H)-benzofuranone

After 2-[(3-methoxyphenyl)methylene]-6-hydroxy-3(2H)-benzofuranone 0.5 g was dissolved in pyridine 5 ml, acetyl chloride 0.172 ml was added, and the mixture was refluxed for 2.5 hours. The reaction mixture was cooled to room temperature, ethyl acetate 50 ml was added, and the mixture was washed with 2N-hydrochloric acid 50 ml twice. After the ethyl acetate solution was dehydrated with anhydrous magnesium sulfate, it was concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for five hours under reduced pressure to obtain the desired compound 371.6 mg.

FAB MASS; 311 (M+1)

$^1$H-NMR (ppm, in CDCl$_3$); 2.33 (3H, s), 3.85 (3H, s), 7.34 (1H, t, J=7.9 Hz), 7.45 (2H, m), 7.78 (1H, d, J=8.2 Hz)

EXAMPLE 27

Synthesis of 2-[(3,4-dimethoxyphenyl)methylene]-6-acetoxy-3(2H)-benzofuranone

After 2-[(3,4-dimethoxyphenyl)methylene]-6-hydroxy-3(2H)-benzofuranone 0.5 g was dissolved in pyridine 5 ml, acetyl chloride 0.2 ml was added, and the mixture was refluxed for two hours. The reaction mixture was cooled to room temperature, ethyl acetate 50 ml was added, and the mixture was washed with 2N-hydrochloric acid 50 ml twice. After the ethyl acetate phase was dehydrated with anhydrous magnesium sulfate, it was concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for four hours under reduced pressure to obtain the desired compound 341.3 mg.

FAB MASS; 341 (M+1)

$^1$H-NMR (ppm, in CDCl$_3$); 2.32 (3H, s), 3.91 (3H, s), 3.93 (3H, s), 6.83 (1H, s), 6.90 (1H, d, J=8.5 Hz), 6.91 (1H, dd, J=8.2, 1.8 Hz), 7.12 (1H, dd, J=1.8, 0.6 Hz), 7.42 (1H, dd, J=8.5, 2.1 Hz), 7.48 (1H, d, J=1.8 Hz), 7.77 (1H, d, J=8.2 Hz)

EXAMPLE 28

Synthesis of 2-[(3,5-dimethoxyphenyl)methylene]-6-acetoxy-3(2H)-benzofuranone

After 2-[(3,5-dimethoxyphenyl)methylene]-6-hydroxy-3(2H)-benzofuranone 0.5 g was dissolved in pyridine 5 ml, acetyl chloride 0.2 ml was added, and the mixture was refluxed for two hours. The reaction mixture was cooled to room temperature, ethyl acetate 50 ml was added, and the ethyl acetate phase was washed with 2N-hydrochloric acid 50 ml twice. After the ethyl acetate solution was dehydrated with anhydrous magnesium sulfate, it was concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for four hours under reduced pressure to obtain the desired compound 249.1 mg.

FAB MASS; 341 (M+1)

$^1$H-NMR (ppm, in CDCl$_3$); 2.32 (3H, s), 3.82 (6H, s), 6.50 (1H, m), 6.77 (1H, s), 6.92 (1H, dd, J=8.2, 1.8 Hz), 7.02 (2H, d, J=2.4 Hz), 7.13 (1H, d, J=1.8 Hz), 7.77 (1H, d, J=8.5 Hz)

EXAMPLE 29
Synthesis of 2-[(3-methyl-4-methoxyphenyl)methylene]-6-acetoxy-3(2H)-benzofuranone After 2-[(3-methyl-4-methoxyphenyl)methylene]-6-hydroxy-3(2H)- benzofuranone 0.5 g was dissolved in pyridine 5 ml, acetyl chloride 0.2 ml was added, and the mixture was refluxed for 1.5 hours. The solution was cooled to room temperature, ethyl acetate 50 ml was added, and the mixture was washed with 2N-hydrochloric acid 50 ml twice. After the ethyl acetate solution was dehydrated with anhydrous magnesium sulfate, it was concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for four hours under reduced pressure to obtain the desired compound 436.6 mg.

FAB MASS; 325 (M+1)
$^1$H-NMR (ppm, in CDCl$_3$); 2.24 (3H, s), 2.32 (3H, s), 3.86 (3H, s), 6.82 (1H, s), 6.86 (1H, d, J=8.5 Hz), 6.90 (1H, d, J=1.8 Hz), 7.68 (1H, s), 7.71 (1H, dd, J=8.2, 2.1 Hz), 7.77 (1H, d, J=8.3 Hz)

EXAMPLE 30
Synthesis of 2-[(3,4-dimethoxyphenyl)methylene]-6-benzoyloxy-3(2H)-benzofuranone After 2-[(3,4-dimethoxyphenyl)methylene]-6-hydroxy-3(2H)-benzofuranone 0.5 g was dissolved in pyridine 5 ml, benzoyl chloride 0.282 ml was added, and the mixture was refluxed for two hours. The reaction mixture was cooled to room temperature, ethyl acetate 50 ml was added, and the mixture was washed with 2N-hydrochloric acid 50 ml twice and with saturated sodium bicarbonate solution 50 ml. After the ethyl acetate solution was dehydrated with anhydrous magnesium sulfate, it was concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for four hours under reduced pressure to obtain the desired compound 294.6 mg.

FAB MASS; 403 (M+1)
$^1$H-NMR (ppm, in CDCl$_3$); 3.91 (3H, s), 3.92 (3H, s), 6.87 (1H, s), 6.92 (1H, d, J=8.5 Hz), 7.06 (1H, dd, J=8.5, 2.1 Hz), 7.28 (1H, d, J=1.5 Hz), 7.45 (1H, m), 7.52 (2H, m), 7.66 (1H, m), 7.85 (1H, d, J=8.2 Hz), 8.19 (2H, m)

EXAMPLE 31
Synthesis of 2-[(3,5-dimethoxyphenyl)methylene]-6-benzoyloxy-3(2H)-benzofuranone After 2-[(3,5-dimethoxyphenyl)methylene]-6-hydroxy-3(2H)-benzofuranone 0.5 g was dissolved in pyridine 5 ml, benzoyl chloride 0.282 ml was added, and the mixture was refluxed for two hours. The reaction mixture was cooled to room temperature, ethyl acetate 50 ml was added and, the ethyl acetate phase was washed with 2N-hydrochloric acid 50 ml twice and with saturated sodium bicarbonate solution 50 ml. After the ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for four hours under reduced pressure to obtain the desired compound 388.5 mg.

FAB MASS; 403 (M+1)
$^1$H-NMR (ppm, in CDCl$_3$); 3.83 (6H, s), 6.52 (1H, br), 6.81 (1H, s), 7.06 (1H, d, J=2.1 Hz), 7.08 (1H, dd, J=8.5, 2.1 Hz), 7.29 (1H, d, J=2.1 Hz), 7.53 (1H, t, J=7.9 Hz), 7.66 (1H, t, J=7.3 Hz), 7.84 (1H, d, J=8.2 Hz), 8.19 (2H, d, J=7.3 Hz)

EXAMPLE 32
Synthesis of 6-benzoyloxy-2-piperonylidene-3(2H)-benzofuranone

After 6-hydroxy-2-piperonylidene-3(2H)-benzofuranone 0.5 g was dissolved in pyridine 5 ml, benzoyl chloride 0.282 ml was added, and the mixture was refluxed for two hours. The reaction mixture was cooled to room temperature, ethyl acetate 50 ml was added, and the mixture was washed with 2N-hydrochloric acid 50 ml twice. The ethyl acetate solution was dehydrated with anhydrous magnesium sulfate and concentrated under reduced pressure. The crude extract was dissolved in ethyl acetate 10 ml and hexane 20 ml, and the precipitated crystals were dried over phosphorous pentoxide at a temperature of 60° C. for six hours under reduced pressure to obtain the desired compound 182.3 mg.

FAB MASS; 387 (M+1)
$^1$H-NMR (ppm, in CDCl$_3$); 6.02 (2H, s), 6.82 (1H, s), 6.86 (1H, d, J=8.2 Hz), 7.06 (1H, dd, J=8.2, 1.8 Hz), 7.27 (1H, d, J=2.4 Hz), 7.29 (1H, m), 7.52 (2H, m), 7.65 (1H, m), 7.83 (1H, d, J=7.9 Hz), 8.19 (2H, d, J=7.9 Hz)

EXAMPLE 33
Synthesis of 2-[(1,4-benzodioxane)-6-methylene]-6-benzoyloxy-3(2H)-benzofuranone After 2-[(1,4-benzodioxane)-6-methylene]-6-hydroxy-3(2H)-benzofuranone 0.5 g was dissolved in pyridine 5 ml, benzoyl chloride 0.282 ml was added, and the mixture was refluxed for 1.5 hours. The reaction mixture was cooled to room temperature, ethyl acetate 50 ml was added, and the mixture was washed with 2N-hydrochloric acid 50 ml once and with saturated sodium bicarbonate solution 50 ml. The ethyl acetate solution was dehydrated with anhydrous magnesium sulfate and concentrated under reduced pressure. The crystals were dried over phosphorous pentoxide at a temperature of 60° C. for two hours under reduced pressure to obtain the desired compound 411.2 mg.

FAB MASS; 401 (M+1)
$^1$H-NMR (ppm, in DMSO-d$_6$); 4.30 (4H, s), 6.87 (1H, s), 6.97 (1H, d, J=8.2 Hz), 7.48 (1H, dd, J=8.5, 2.1 Hz), 7.55 (1H, d, J=1.8 Hz), 7.62 (2H, m), 7.76 (1H, m), 7.86 (1H, d, J=8.2 Hz), 7.83 (2H, dd, J=8.2, 1.2 Hz)

EXAMPLE 34
Synthesis of 2-[(3-methyl-4-methoxyphenyl)methylene]-6-benzoyloxy-3(2H)-benzofuranone After 2-[(3-methyl-4-methoxyphenyl)methylene]-6-hydroxy-3(2H)-benzofuranone 0.5 g was dissolved in pyridine 5 ml, benzoyl chloride 0.282 ml was added, and the mixture was refluxed for 1.5 hours. The reaction mixture was cooled to room temperature, ethyl acetate 50 ml was added, and the mixture was washed with 2N-hydrochloric acid 50 ml and with saturated sodium bicarbonate solution 50 ml. The ethyl acetate solution was dehydrated with anhydrous magnesium sulfate and concentrated under reduced pressure. The crude extract was dissolved in hexane 10 ml and ethyl acetate 5 ml, and the precipitated crystals were filtered and dried over phosphorous pentoxide at a temperature of 60° C. for five hours under reduced pressure to obtain the desired compound 321.6 mg.

FAB MASS; 387 (M+1)

$^1$H-NMR (ppm, in CDCl$_3$); 2.25 (3H, s), 3.87 (3H, s), 6.85 (1H, s), 6.97 (1H, d, J=8.5 Hz), 7.05 (1H, dd, J=8.2, 1.8 Hz), 7.29 (1H, d, J=1.8 Hz), 7.62 (2H, m), 7.76–7.84 (2H, m), 7.82 (1H, d, J=8.2 Hz), 7.83 (2H, dd, J=7.9, 1.2 Hz)

EXAMPLE 35
Synthesis of 2-[(3-methoxyphenyl)methylene]-6-benzoyloxy-3(2H)-benzofuranone After 2-[(3-methoxyphenyl)methylene]-6-hydroxy-3 (2H)-benzofuranone 0.5 g was dissolved in pyridine 5 ml, benzoyl chloride 0.282 ml was added, and the mixture was refluxed for 1.5 hours. The reaction mixture was cooled to room temperature, ethyl acetate 50 ml was added, and the mixture was washed with 2N-hydrochloric acid 50 ml once and with saturated sodium bicarbonate solution 50 ml. The ethyl acetate solution was dehydrated with anhydrous magnesium sulfate and concentrated under reduced pressure. The resulting powder was dissolved in hexane 10 ml and ethyl acetate 5 ml, and the precipitated crystals were filtered and dried over phosphorous pentoxide at a temperature of 60° C. for four hours under reduced pressure to obtain the desired compound 221.5 mg.

FAB MASS; 373 (M+1)

$^1$H-NMR (ppm, in CDCl$_3$); 3.85 (3H, s), 6.85 (1H, s), 6.94 (1H, dd, J=8.5, 2.7 Hz), 7.05 (1H, dd, J=8.2, 1.8 Hz), 7.28–7.67 (7H, m), 7.84 (1H, d, J=8.2 Hz), 7.99 (2H, dd, J=7.9, 1.2 HZ)

EXAMPLE 36
Synthesis of 2-[(4-methoxyphenyl methylene]-6-benzoyloxy-3(2H)-benzofuranone After 2-[(4-methoxyphenyl)methylene]-6-hydroxy-3 (2H)-benzofuranone 0.5 g was dissolved in pyridine 5 ml, benzoyl chloride 0.282 ml was added, and the mixture was refluxed for 1.5 hours. The reaction mixture was cooled to room temperature, ethyl acetate 50 ml was added, and the mixture was washed with 2N-hydrochloric acid 50 ml and with saturated sodium bicarbonate solution 50 ml. The ethyl acetate solution was dehydrated with anhydrous magnesium sulfate and concentrated under reduced pressure. The resulting crystals were dried over phosphorous pentoxide at a temperature of 60° C. for four hours under reduced pressure to obtain the desired compound 200.5 mg.

FAB MASS; 373 (M+1)

$^1$H-NMR (ppm, in CDCl$_3$); 3.84 (3H, s), 6.87 (1H, s), 6.94 (2H, d, J=8.8 Hz), 7.05 (1H, dd, J=8.2, 1.8 Hz), 7.27 (1H, d, J=1.5 Hz), 7.50–7.87 (6H, m), 7.99 (2H, m)

EXAMPLE 37
Synthesis of 2-[(4-methoxyphenyl)methylene]-6-propionyloxy-3(2H)-benzofuranone After 2-[(4-methoxyphenyl)methylene]-6-hydroxy-3 (2H)-benzofuranone 0.5 g was dissolved in pyridine 5 ml, propionyl chloride 0.218 ml was added, and the mixture was refluxed for 1.5 hours. The reaction mixture was cooled to room temperature, ethyl acetate 50 ml was added, and the mixture was washed with 2N-hydrochloric acid 50 ml once, saturated sodium bicarbonate solution 50 ml, and a saturated salt solution 50 ml. The ethyl acetate solution was dehydrated with anhydrous magnesium sulfate and concentrated under reduced pressure. The crude extract was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were recrystallized with ethyl acetate 4 ml/hexane 10 ml and filtered. The crystals were dried over phosphorous pentoxide at a temperature of 60° C. for five hours under reduced pressure to obtain the desired compound 251.6 mg.

FAB MASS; 325 (M+1)

$^1$H-NMR (ppm, in CDCl$_3$); 1.27 (3H, t, J=7.6 Hz), 2.61 (2H, q, J=7.6 Hz), 3.85 (3H, s), 6.83 (1H, s), 6.92 (2H, m), 7.14 (1H, dd, J=2.1, 0.6 Hz), 7.34 (1H, t, J=7.9 Hz), 7.43 (2H, m), 7.79 (2H, d, J=8.8 Hz)

EXAMPLE 38
Synthesis of 2-[(3-methoxyphenyl)methylene]-6-propionyloxy-3(2H--benzofuranone After 2-[(3-methoxyphenyl)methylene]-6-hydroxy-3 (2H)-benzofuranone 0.5 g was dissolved in pyridine 5 ml, propionyl chloride 0.218 ml was added, and the mixture was refluxed for 1.5 hours. The reaction mixture was cooled to room temperature, ethyl acetate 50 ml was added, and this solution was washed with 2N-hydrochloric acid 50 ml once, saturated sodium bicarbonate 50 ml, and a saturated salt solution 50 ml. The ethyl acetate solution was dehydrated with anhydrous magnesium sulfate and concentrated under reduced pressure. The crude extract was fractionated by silica gel column chromatography (silica gel: 50 g, eluted with solvent 400 ml of hexane:ethyl acetate=1:1) and the fraction was concentrated to dryness at a temperature of 40° C. under reduced pressure to obtain crystals. The crystals were recrystallized with ethyl acetate 5 ml/hexane 5 ml and filtered. The crystals were dried over phosphorous pentoxide at a temperature of 60° C. for five hours under reduced pressure to obtain the desired compound 277.8 mg.

FAB MASS; 325 (M+1)

$^1$H-NMR (ppm, in CDCl$_3$); 1.27 (3H, t, J=7.6 Hz), 2.61 (2H, q, J=7.6 Hz), 3.85 (3H, s), 6.83 (1H, s), 6.92 (2H, m), 7.14 (1H, d, J=1.5 Hz), 7.34 (1H, t, J=7.9 Hz), 7.45 (2H, m), 7.79 (2H, d, J=8.8 Hz)

EXAMPLE 39
Synthesis of 2-[(3-methyl-4-methoxyphenyl)methylene]6-propionyloxy-3(2H)-benzofuranone After 2-[(3-methyl-4-methoxyphenyl)methylene]-6-hydroxy-3(2H)-benzofuranone 0.525 g was dissolved in pyridine 5 ml, propionyl chloride 0.218 ml was added, and the mixture was refluxed for 1.5 hours. The reaction mixture was cooled to room temperature, ethyl acetate 50 ml was added, and the mixture was washed with 2N-hydrochloric acid 50 ml, saturated salt solution 50 ml, saturated sodium bicarbonate solution 50 ml, and saturated sodium chloride solution 50 ml. The ethyl acetate solution was dehydrated with anhydrous magnesium sulfate and concentrated under reduced pressure. The residue was fractionated by silica gel column chromatography (silica gel: 50 g, eluted with solvent 350 ml of hexane:ethyl acetate=1:1) and concentrated to dryness at a temperature of 40° C. under reduced pressure to obtain crystals. The crystals were recrystallized with ethyl acetate 2 ml/hexane 5 ml and filtered. The crystals were dried over phosphorous pentoxide at a temperature of 60° C. for five hours under reduced pressure to obtain the desired compound 322.9 mg.

FAB MASS; 339 (M+1)

$^1$H-NMR (ppm, in CDCl$_3$); 1.26 (3H, t, J=7.6 Hz), 2.24 (3H, s), 2.61 (2H, q, J=7.6 Hz), 3.86 (3H, dd, J=8.2, 2.4 Hz), 7.15 (1H, d, J=1.8 Hz), 7.69 (2H, m), 7.67 (1H, d, J=8.2 Hz)

EXAMPLE 40
Synthesis of 2-[(3,5-dimethoxyphenyl)methylene]-6-propionyloxy-3(2H)-benzofuranone After 2-[(3,5-dimethoxyphenyl)methylene]-6-hydroxy-3 (2H)-benzofuranone 0.525 g was dissolved in pyridine 5 ml, propionyl chloride 0.218 ml was added, and the mixture was refluxed for 1.5 hours. The reaction mixture was cooled to room temperature, ethyl acetate 50 ml was added, and the mixture was washed with 2N-hydrochloric acid 50 ml, saturated sodium bicarbonate solution 50 ml, and a saturated sodium chloride solution 50 ml. The ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were recrystallized with ethyl acetate 5 ml/hexane 10 ml and filtered. The crystals were dried over phosphorous pentoxide at a temperature of 60° C. for five hours under reduced pressure to obtain the desired compound 275.1 mg.

FAB MASS; 355 (M+1)
$^1$H-NMR (ppm, in CDCl$_3$); 1.27 (3H, t, J=7.6 Hz), 2.61 (2H, q, J=7.6 Hz), 3.82 (6H, s), 6.50 (1H, t, J=2.4 Hz), 6.76 (1H, s), 6.92 (1H, dd, J=8.2, 1.8 Hz), 7.03 (2H, d, J=2.1 Hz), 7.13 (1H, d, J=1.5 Hz), 7.77 (1H, d, J=8.8 Hz)

EXAMPLE 41

Synthesis of 2-[(3,4-dimethoxyphenyl)methylene]-6-propionyloxy-3(2H)-benzofuranone After 2-[(3,4-dimethoxyphenyl)methylene]-6-hydroxy-3 (2H)-benzofuranone 0.525 g was dissolved in pyridine 5 ml, propionyl chloride 0.218 ml was added, and the mixture was refluxed for 1.5 hours. The reaction mixture was cooled to room temperature, ethyl acetate 50 ml was added, and the mixture was washed with 2N-hydrochloric acid 50 ml, saturated sodium bicarbonate solution 50 ml, and a saturated sodium chloride solution 50 ml. The ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for five hours under reduced pressure to obtain the desired compound 311.6 mg.

FAB MASS; 355 (M+1)
$^1$H-NMR (ppm, in CDCl$_3$); 1.27 (3H, t, J=7.6 Hz), 2.62 (2H, q, J=7.6 Hz), 3.92 (3H, s), 6.84 (1H, s), 6.92 (2H, m), 7.14 (1H, d, J=2.4 Hz), 7.43 (1H, dd, J=8.2, 1.8 Hz), 7.50 (1H, d, J=2.2 Hz), 7.79 (1H, d, J=8.2 Hz)

EXAMPLE 42

Synthesis of 6-propionyloxy-2-piperonylidene-3(2H)-benzofuranone

After 6-hydroxy-2-piperonylidene-3(2H)-benzofuranone 0.5 g was dissolved in pyridine 5 ml, propionyl chloride 0.218 ml was added, and the mixture was refluxed for 1.5 hours. The reaction mixture was cooled to room temperature, ethyl acetate 50 ml was added, and the mixture was washed with 2N-hydrochloric acid 50 ml, a saturated sodium chloride solution 50 ml, saturated sodium bicarbonate solution 50 ml, and a saturated salt solution 50 ml. The ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were recrystallized with ethyl acetate 1 ml/hexane 10 ml and filtered. The crystals were dried over phosphorous pentoxide at a temperature of 60° C. for four hours under reduced pressure to obtain the desired compound 300.6 mg.

FAB MASS; 339 (M+1)
$^1$H-NMR (ppm, in CDCl$_3$); 1.25 (3H, t, J=7.6 Hz), 2.59 (2H, q, J=7.6 Hz), 5.98 (2H, s), 6.75 (1H, s), 6.81 (1H, d, J=7.9 Hz), 6.89 (1H, dd, J=8.2, 2.4 Hz), 7.10 (1H, d, J=2.4 Hz), 7.24 (1H, dd, J=8.2, 1.8 Hz), 7.50 (1H, d, J=1.2 Hz), 7.74 (1H, d, J=8.2 Hz)

EXAMPLE 43

Synthesis of 2-[(1,4-benzodioxane)-6-methylene]-6-propionyloxy-3(2H)-benzofuranone After 2-[(1,4-benzodioxane)-6-methylene]-6-hydroxy-3 (2H)-benzofuranone 0.5 g was dissolved in pyridine 5 ml, propionyl chloride 0.218 ml was added, and the mixture was refluxed for 1.5 hours. The reaction mixture was cooled to room temperature, 2N-hydrochloric acid 50 ml was added, and the mixture was extracted with ethyl acetate 50 ml and the ethyl acetate solution was washed with saturated sodium bicarbonate solution 50 ml. The ethyl acetate solution was dehydrated with anhysrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dried over phosphorous pentoxide at a temperature of 60° C. for two hours under reduced pressure to obtain the desired compound 272.9 mg.

FAB MASS; 353 (M+1)
$^1$H-NMR (ppm, in CDCl$_3$); 1.26 (3H, t, J=7.6 Hz), 2.60 (2H, q, J=7.6 Hz), 4.26 (2H, m), 6.75 (1H, s), 6.87 (1H, d, J=8.2 Hz), 6.90 (1H, dd, J=8.5, 2.1 Hz), 7.11 (1H, d, J=1.8 Hz), 7.32 (1H, dd, J=8.5, 2.1 Hz), 7.47 (1H, d, J=2.1 Hz), 7.74 (1H, d, J=8.2 Hz)

EXAMPLE 44

Synthesis of 2-[(4-methoxyphenyl)methylene]-6-isopropyloxy-3(2H)-benzofuranone

To a solution of 2-[(4-methoxyphenyl)methylene]-6-hydroxy-3(2H)-benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was washed with a saturated sodium chloride solution 50 ml twice, dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 1 ml and hexane 10 ml, and the solution was allowed to stand at room temperature for four hours. The precipitated crystals were filtered and dried over phosphorous pentoxide at a temperature of 60° C. for four hours under reduced pressure to obtain the desired compound 462.9 mg.

FAB MASS: 311(M+1)
$^1$H-NMR (ppm, Hz, in CDCl$_3$); 1.38 (6H, d, J=7.6 Hz), 3.83 (3H, s), 4.64 (1H, q, J=7.6 Hz), 6.67 (2H, m), 6.76 (1H, s), 6.93 (2H, d, J=7.0 Hz), 7.64 (1H, d, J=8.2 Hz), 7.81 (2H, d, J=7.0 Hz)

EXAMPLE 45

Synthesis of 2-[(3-methoxyphenyl)methylene]-6-isopropyloxy-3(2H)-benzofuranone

To a solution of 2-[(3-methoxyphenyl)methylene]-6-hydroxy-3(2H)-benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was washed with a saturated sodium chloride solution 20 ml twice, dehydrated with anhysrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 2 ml and hexane 10 ml, and the solution was allowed to stand at room temperature for four hours. The precipitated crystals were filtered and dried over phosphorous pentoxide at a temperature of 60° C. for four hours under reduced pressure to obtain the desired compound 187.2 mg.

$^1$H-NMR (ppm, Hz, in CDCl$_3$); 1.38 (6H, d, J=7.6 Hz), 3.84 (3H, s), 4.65 (1H, q, J=7.6 Hz), 6.67 (2H, m), 6.74 (1H, s), 6.91 (1H, d, J=8.2 Hz), 7.32 (1H, t, J=7.9 Hz), 7.44 (2H, m), 7.65 (1H, d, J=8.5 Hz)

EXAMPLE 46

Synthesis of 2-[(3,4-dimethoxyphenyl)methylene]-6-isopropyloxy-3(2H)-benzofuranone To a solution of 2-[(3,4-dimethoxyphenyl)methylene]-6-hydroxy-3(2H)-benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 30 ml twice. The ethyl acetate solution was washed with a saturated sodium chloride solution 50 ml twice, dehydrated with anhydrous magnesium sulfate and concentrated under reduced pressure. The residue was fractionated by silica gel column chromatography (silica gel: 50 g, eluted with solvent 500 ml of hexane-:ethyl acetate=1:1) and the fraction was concentrated to dryness at a temperature of 40° C. under reduced pressure to obtain crystals. The crystals were dissolved in ethyl acetate 2 ml and hexane 5 ml, and the solution was allowed to stand at room temperature for four hours. The precipitated crystals were filtered and dried over phosphorous pentoxide at a temperature of 60° C. for four hours under reduced pressure to obtain the desired compound 622.7 mg.

FAB MASS: 341(M+1)

$^1$H-NMR (ppm, Hz, in CDCl$_3$); 1.36 (6H, d, J=7.6 Hz), 3.88 (3H, s), 3.92 (3H, s), 4.64 (1H, q, J=7.6 Hz), 6.65 (2H, m), 6.71 (1H, s), 6.87 (1H, d, J=8.2 Hz), 7.41 (1H, t, J=8.2, 1.8 Hz), 7.43 (1H, d, J=1.8 Hz), 7.63 (1H, d, J=9.5 Hz)

EXAMPLE 47

Synthesis of 2-[(3,5-dimethoxyphenyl)methylene]-6-isopropyloxy-3(2H)-benzofuranone To a solution of 2-[(3,5-dimethoxyphenyl)methylene]-6-hydroxy-3(2H)-benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate= 1:1) and the fraction was concentrated to dryness at a temperature of 40° C. under reduced pressure to -obtain crystals. The crystals were dissolved in ethyl acetate 2 ml and hexane 10 ml, and the solution was allowed to stand at room temperature for four hours. The precipitated crystals were filtered and dried over phosphorous pentoxide at a temperature of 60° C. for four hours under reduced pressure to obtain the desired compound 316.1 mg.

FAB MASS: 341(M+1)

$^1$H-NMR (ppm, Hz, in CDCl$_3$); 1.38 (6H, d, J=7.6 Hz), 3.83 (3H, s), 4.65 (1H, q, J=7.6 Hz), 6.48 (1H, m), 6.67 (3H, m), 7.03 (2H, d, J=2.1 Hz), 7.65 (1H, t, J=8.8 Hz)

EXAMPLE 48

Synthesis of 2-[(3-methyl-4-methoxyphenyl)methylene]-6-isopropyloxy-3(2H)-benzofuranone To a solution of 2-[(3-methyl-4-methoxyphenyl)methylene]-6-hydroxy-3(2H)-benzofuranone 0.5 g, potassium carbonate 0.61 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 2 ml and hexane 5 ml, and the solution was allowed to stand at room temperature for four hours. The precipitated crystals were filtered and dried over phosphorous pentoxide at a temperature of 60° C. for four hours under reduced pressure to obtain the desired compound 275.1 mg.

FAB MASS: 325(M+1)

$^1$H-NMR (ppm, Hz, in CDCl$_3$); 1.40 (6H, d, J=7.6 Hz), 2.25 (3H, s), 3.86 (3H, s), 4.66 (1H, q, J=7.6 Hz), 6.48 (1H, d, J=8.5, 2.1 Hz), 6.71 (1H, d, J=2.1 Hz), 6.75 (1H, s), 7.86 (1H, d, J=8.5 Hz), 7.69 (3H, m)

EXAMPLE 49

Synthesis of 2-[(1,4-benzodioxane)-6-methylene]-6-isopropyloxy-3(2H)-benzofuranone

PRODUCTION EXAMPLE 1

To a solution of 2-[(1,4-benzodioxane)-6-methylene]-6-hydroxy-3(2H)- benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was washed with a saturated sodium chloride solution 50 ml twice, dehydrated with anhydrous magnesium sulfate and concentrated under reduced pressure. The residue was fractionated by silica gel column chromatography (silica gel: 50 g, eluted with solvent 500 ml of hexane-:ethyl acetate=1:1) and the fraction was concentrated to dryness at a temperature of 40° C. under reduced pressure to obtain crystals. The crystals were dissolved in ethyl acetate 4 ml and hexane 10 ml, and the solution was allowed to stand at room temperature for two hours. The precipitated crystals were filtered and dried over phosphorous pentoxide at a temperature of 60° C. for four hours under reduced pressure to obtain the desired compound 422.7 mg.

FAB MASS: 339(M+1)

$^1$H-NMR (ppm, Hz, in CDCl$_3$); 1.39 (6H, d, J=7.6 Hz), 4.28 (4H, m), 4.62 (1H, q, J=7.6 Hz), 6.48 (3H, m), 6.87 (1H, d, J=8.2 Hz), 7.30 (1H, dd, J=8.5, 2.1 Hz), 7.50 (1H, d, J=1.8 Hz), 7.63 (1H, d, J=8.5 Hz)

PRODUCTION EXAMPLE 2

To dimethylformamide 100 ml, 6-hydroxy-2H-benzofuranon-3-one 10 g and potassium carbonate 27.6 g were added. Then 2-bromopropane 11.8 ml was added and stirred for an hour at a temperature of 60° C. After the mixture was cooled, ethyl acetate 200 ml was added. The ethyl acetate solution was washed with water 100 ml twice and a saturated sodium chloride solution 100 ml twice, dehydrated with anhydrous magnesium sulfate and concentrated under reduced pressure at 40° C. to obtain oil. The residue was fractionated by silica gel column chromatography (silica gel: 250 g, eluted with solvent of hexane:ethyl acetate=1:1). To the fraction, hexane 50 ml was added, and the solution was allowed to stand at room temperature for two hours. The precipitated crystals were filtered and dried over phosphorous pentoxide at a temperature of 60° C. for seven hours to obtain 6-isopropyloxy-2H-benzofuran-3-one 6.37 g.

FAB MASS: 193(M+1)

$^1$H-NMR (ppm, Hz, in CDCl$_3$); 1.29 (6H, d), 4.73–4.79 (3H, m), 6.63 (1H, dd, J=8.5, 2.1 Hz), 6.77 (1H, d, J=1.5 Hz), 7.48 (1H, d, J=8.5 Hz)

After the resulting 6-isopropyloxy-2H-benzofuran-3-one 0.5 g and 1,4-benzodioxan-6-carboxyaldehyde 0.6 g were dissolved in acetic acid 10 ml, concentrated hydrochloric acid 0.5 ml was added, and the mixture was stirred for 18 hours. Precipitated crystals were filtered, and dissolved in methanol 50 ml. Water 100 ml was added to the methanol solution, the desired compound was extracted with ethyl acetate 100 ml twice. After washing the ethyl acetate solution with a saturated sodium bicarbonate solution 100 ml twice and water 100 ml twice, the solution was dehydrated with anhydrous magnesium sulfate. The solution was concentrated at a temperature of 40° C. under reduced pressure to obtain oil. Methanol 20 ml was added to the oil, the precipitated crystals were filtered, and the crystals were filtered and dried over phosphorous pentoxide at a temperature of 60° C. for four hours to obtain the desired compound 0.75 g.

PRODUCTION EXAMPLE 3

After 6-isopropyloxy-2H-benzofuran-3-one 0.5 g and 1,4-benzodioxane-6-carboxyaldehyde 0.6 g were suspended in ethanol 10 ml, two drops of piperidine was added, and the mixture was stirred for four hours. The precipitated crystals were filtered, washed with ethanol 10 ml twice, and dried over phosphorous pentoxide for four hours to obtain the desired compound 0.37 g.

EXAMPLE 50

Synthesis of 6-isopropyloxy-2-piperonylidene-3(2H)-benzofuranone

To a solution of 6-hydroxy-2-piperonylidene 3(2H)-benzofuranone 0.5 g, potassium carbonate 0.58 g and dimethylformamide 5 ml, 2-bromopropane 0.306 g was added. After the mixture was refluxed for 2.5 hours, water 50 ml was added. The resulting compound was extracted with ethyl acetate 50 ml twice. The ethyl acetate solution was washed with a saturated sodium chloride solution 50 ml twice, dehydrated with anhydrous magnesium sulfate and concentrated under reduced pressure. The crude extract was fractionated by silica gel column chromatography (silica gel: 50 g, eluted with solvent 500 ml of hexane:ethyl acetate= 1:1) and the fraction was concentrated to dryness at a temperature of 40° C. under reduced pressure to obtain crystals. The crystals were dissolved in ethyl acetate 5 ml and hexane 10 ml, and the solution was allowed to stand at room temperature for two hours. The precipitated crystals were filtered and dried over phosphorous pentoxide at a temperature of 60° C. for four hours under reduced pressure to obtain the desired compound 519.6 mg.

FAB MASS: 325(M+1)

$^1$H-NMR (ppm, Hz, in CDCl$_3$); 1.39 (6H, d, J=7.6 Hz), 6.00 (2H, s), 6.48 (3H, m), 6.87 (1H, d, J=8.2 Hz), 7.30 (1H, dd, J=8.5, 1.8 Hz), 7.52 (1H, d, J=1.5 Hz), 7.64 (1H, d, J=8.8 Hz)

EXAMPLE 51

Synthesis of 2-[(3-methyl-4-methoxyphenyl)methylene]-6-methoxy-3(2H)-benzofuranone To a solution of 2-[(3-methyl-4-methoxyphenyl) methylene]-6-hydroxy-3(2H)-benzofuranone 0.477 g, potassium carbonate 0.583 g and dimethylformamide 5 ml, methyl p-toluenesulfonate 0.314 g was added. After the mixture was stirred for two hours at a temperature of 60° C., water 100 ml was added. The resulting compound was extracted with ethyl acetate 50 ml twice. The ethyl acetate solution was washed with a saturated sodium chloride solution 50 ml twice, dehydrated with anhydrous magnesium sulfate, and concentrated at a temperature of 40° C. under reduced pressure to obtain crude powder. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 2 ml and hexane 10 ml, and the solution was allowed to stand at room temperature for two hours. The precipitated crystals were filtered and dried over phosphorous pentoxide at a temperature of 60° C. for four hours under reduced pressure to obtain the desired compound 371.6 mg.

FAB MASS: 297(M+1)

$^1$H-NMR (ppm, Hz, in CDCl$_3$); 2.23 (3H, s), 3.84 (3H, s), 3.87 (3H, s), 6.69 (1H, dd, J=8.5, 2.1 Hz), 6.71 (1H, d, J=1.8 Hz), 6.73 (1H, s), 6.83 (1H, d, J=8.5 Hz), 7.64 (3H, m)

EXAMPLE 52

Synthesis of 2-[(1,4-benzodioxane)-6-methylene]-6-methoxy-3(2H)-benzofuranone

To a solution of 2-[(1,4-benzodioxane)-6-methylene]-6-hydroxy-3(2H)-benzofuranone 0.5 g, potassium carbonate 0.58 g and dimethylformamide 5 ml, methyl p-toluene sulfonate 0.314 g was added. After the mixture was stirred for two hours at a temperature of 60° C., water 100 ml was added. The resulting compound was extracted with ethyl acetate 50 ml twice. The ethyl acetate solution was washed with a saturated sodium chloride solution 50 ml twice, dehydrated with anhydrous magnesium sulfate and concentrated under reduced pressure. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 2 ml and hexane 10 ml, and the solution was allowed to stand at room temperature for two hours. The precipitated crystals were filtered and dried over phosphorous pentoxide at a temperature of 60° C. for four hours under reduced pressure to obtain the desired compound 226.2 mg.

FABB MASS: 311(M+1)

$^1$H-NMR (ppm, Hz, in CDCl$_3$); 3.89 (3H, s), 4.28 (4H, m), 4.72 (3H, m), 6.88 (1H, d, J=8.2 Hz), 7.31 (1H, dd, J=8.2, 2.1 Hz), 7.49 (1H, d, J=2.1 Hz), 7.66 (1H, d, J=8.2 Hz)

EXAMPLE 53
Synthesis of 2-[(3-methoxyphenyl)methylene]-6-methoxy-3 (2H)-benzofuranone To a solution of 2-[(3-methoxyphenyl)methylene]-6-hydroxy-3(2H)-benzofuranone 0.452 g, potassium carbonate 0.583 g and dimethylformamide 5 ml, methyl p-toluene sulfonate 0.314 g was added. After the mixture was stirred for two hours at a temperature of 60° C., water 100 ml was added, and the mixture was extracted with ethyl acetate 50 ml twice. The ethyl acetate solution was washed with a saturated sodium chloride solution 50 ml twice, dehydrated with anhydrous magnesium sulfate, filtered and concentrated at a temperature of 40° C. under reduced pressure to obtain crude powder. The residue was fractionated by silica gel column chromatography (silica gel: 50 g, eluted with solvent 500 ml of hexane:ethyl acetate=1:1) and the fraction was concentrated to dryness at a temperature of 40° C. under reduced pressure to obtain crystals. The crystals were dissolved in ethyl acetate 2 ml and hexane 10 ml, and the solution was allowed to stand at room temperature for two hours. The precipitated crystals were filtered and dried over phosphorous pentoxide at a temperature of 60° C. for four hours under reduced pressure to obtain the desired compound 377.2 mg.

FAB MASS: 283(M+1)
$^1$H-NMR (ppm, Hz, in CDCl$_3$); 3.84 (3H, s), 3.89 (3H, s), 6.72 (3H, m), 6.91 (1H, m), 7.33 (1H, m), 7.42 (2H, m), 7.66 (1H, d, J=8.5 Hz)

EXAMPLE 54
Synthesis of 2-[(2,4-dimethoxyphenyl)methylene]-6-hydroxy-3(2H)-benzofuranone After 6-hydroxy-2H-benzofuran-3-one 1 g and 2,6-dimethoxybenzaldehyde 1.23 g were dissolved in methanol 75 ml, concentrated hydrochloric acid 50 ml was added, and the mixture was refluxed for 1.5 hours. After the solution was cooled to room temperature, water 400 ml was added. The precipitated crystals were filtered, and dried over phosphorous pentoxide at a temperature of 60° C. for four hours under reduced pressure to obtain the desired compound 0.95 g.

FAB MASS; 299 (M+1)
$^1$H-NMR (ppm, in DMSO-d$_6$); 3.83 (3H, s), 3.89 (3H, s), 6.63 (1H, d, J=2.4 Hz), 6.67 (1H, dd, J=8.8, 2.4 Hz), 6.67 (1H, dd, J=8.8, 2.1 Hz), 6.78 (1H, d, J=1.8 Hz), 7.01 (1H, s), 7.57 (1H, d, J=8.5 Hz), 8.09 (1H, d, J=8.8 Hz)

EXAMPLE 55
Synthesis of 2-[(3-methoxy-4-propyloxyphenyl)methylene]-6-hydroxy-3(2H)-benzofuranone After 6-hydroxy-2H-benzofuran-3-one 1 g and 3-methoxy-4-propyloxybenzaldehyde 1.55 g were dissolved in methanol 70 ml, concentrated hydrochloric acid 50 ml was added, and the mixture was refluxed for two hours. After the solution was cooled to room temperature, the precipitated crystals were filtered and dried over phosphorous pentoxide at a temperature of 60° C. for four hours under reduced pressure to obtain the desired compound 0.74 g.

FAB MASS; 327 (M+1)
$^1$H-NMR (ppm, in DMSO-d$_6$); 0.97 (3H, t), 1.37 (2H, m), 3.83 (3H, s), 3.97 (2H, m), 6.70 (2H, dd, J=8.5, 2.1 Hz), 6.75 (1H, s), 6.79 (1H, d, J=1.8 Hz), 7.04 (1H, d, J=7.9 Hz), 7.53–7.55 (2H, m), 7.59 (1H, d, J=8.2 Hz)

EXAMPLE 56
Synthesis of 2-[(3-methoxy-4-butoxyphenyl)methylene]-6-hydroxy -3(2H)-benzofuranone After 6-hydroxy-2H-benzofuran-3-one 1 g and 3-methoxy-4-butoxybenzaldehyde 1.66 g were dissolved in methanol 60 ml, concentrated hydrochloric acid 50 ml was added, and the mixture was refluxed for 2.5 hours. After the solution was cooled to room temperature, the precipitated crystals were filtered and dried over phosphorous pentoxide at a temperature of 60° C. for four hours under reduced pressure to obtain the desired compound 0.97 g.

FAB MASS; 341 (M+1)
$^1$H-NMR (ppm, in DMSO-d$_6$); 0.90 (3H, t), 1.40 (2H, m), 1.68 (2H, s), 3.82 (3H, s), 3.98 (2H, m), 6.70 (2H, dd, J=8.5, 2.1 Hz), 6.73 (1H, s), 6.78 (1H, d, J=2.1 Hz), 7.01 (1H, d, J=8.2 Hz), 7.50–7.53 (2H, m), 7.58 (1H, d, J=8.5 Hz)

EXAMPLE 57
Synthesis of 2-[(3-methoxy-4-pentyloxyphenyl)methylene]-6-hydroxy-3(2H)-benzofuranone After 6-hydroxy-2H-benzofuran-3-one 1 g and 3-methoxy-4-pentyloxybenzaldehyde 1.77 g were dissolved in methanol 60 ml, concentrated hydrochloric acid 50 ml was added, and the mixture was refluxed for 2.5 hours. After the solution was cooled to room temperature, the precipitated crystals were filtered and dried over phosphorous pentoxide at a temperature of 60° C. for four hours under reduced pressure to obtain the desired compound 1.25 g.

FAB MASS; 355 (M+1)
$^1$H-NMR (ppm, in DMSO-d$_6$); 0.85 (3H, t), 1.33 (4H, m), 1.70 (2H, m), 3.82 (3H, s), 3.97 (2H, m), 6.70 (2H, dd, J=8.2, 1.8 Hz), 6.73 (1H, s), 6.78 (1H, d, J=2.1 Hz), 7.01 (1H, d, J=8.5 Hz), 7.50–7.53 (2H, m), 7.59 (1H, d, J=8.2 Hz)

EXAMPLE 58
Synthesis of 2-[(3-methoxy-4-hexyloxyphenyl)methylene]-6-hydroxy-3(2H)-benzofuranone After 6-hydroxy-2H-benzofuran-3-one 1 g and 3-methoxy-4-hexyloxybenzaldehyde 1.88 g were dissolved in methanol 60 ml, concentrated hydrochloric acid 50 ml was added, and the mixture was refluxed for 2.5 hours. After the solution was cooled to room temperature, the precipitated crystals were filtered and dried over phosphorous pentoxide at a temperature of 60° C. for four hours under reduced pressure to obtain the desired compound 1.34 g.

FAB MASS; 369 (M+1)
$^1$H-NMR (ppm, in DMSO-d$_6$); 0.83 (3H, t), 1.26 (4H, m), 1.37 (4H, m), 1.67 (2H, m), 3.82 (3H, s), 3.96 (2H, m), 6.70 (2H, dd, J=8.5, 1.8 Hz), 6.73 (1H, s), 6.78 (1H, d, J=2.1 Hz), 7.01 (1H, d, J=8.2 Hz), 7.50–7.53 (2H, m), 7.59 (1H, d, J=8.5 Hz)

EXAMPLE 59
Synthesis of 2-[(1,4-benzodioxane)-6-methylene]-6-ethoxy-3(2H)-benzofuranone After 2-[(1,4-benzodioxane)-6-methylene]-6-hydroxy-3 (2H)-benzofuranone 1.0 g and potassium carbonate 1.95 g were added to dimethylformamide 10 ml, ethyl iodide 0.48 ml was added, and the mixture was reacted at a temperature of 100° C. for two hours. After the solution was cooled to room temperature, ethyl acetate 100 ml was added, and the mixture was washed with water 50 ml three times and a saturated salt solution 50 ml twice. The ethyl acetate solution was dehydrated with anhydrous magnesium sulfate, and concentrated to 40 ml at a temperature of 40° C. under reduced pressure. The precipitated crystals were filtered and dried over phosphorous pentoxide at a temperature of 60° C. for four hours under reduced pressure to obtain the desired compound 0.74 g.

FAB MASS; 325 (M+1)
$^1$H-NMR (ppm, in CDCl$_3$); 1.44 (3H, t), 4.10 (2H, q), 4.28 (4H, m), 6.68 (3H, m), 6.88 (1H, d, J=8.5 Hz), 7.30 (1H, dd, J=8.5, 2.1 Hz), 7.49 (1H, d, J=1.8 Hz), 7.63 (1H, d, J=8.5 Hz)

EXAMPLE 60
Synthesis of 2-[(1,4-benzodioxane)-6-methylene]-6-propyloxy-3(2H)-benzofuranone After 2-[(1,4-benzodioxane)-6-methylene]-6-hydroxy-3(2H)-benzofuranone 1.0 g and potassium carbonate 1.95 g were added to dimethylformamide 10 ml, propyl iodide 0.59 ml was added, and the mixture was reacted at a temperature of 100° C. for two hours. After the solution was cooled to room temperature, water 100 ml was added, and the mixture was extracted with ethyl acetate 50 ml twice. The ethyl acetate solution was washed with water 100 ml twice and a saturated sodium chloride solution 50 ml twice. The ethyl acetate solution was dehydrated with anhydrous magnesium sulfate, and concentrated at a temperature of 40° C. under reduced pressure. The resulting crystals were dissolved at a temperature of 60° C. by adding ethyl acetate 15 ml and allowed to stand for two hours at a temperature of 5° C. . The precipitated crystals were filtered and dried over phosphorous pentoxide at a temperature of 60° C. for four hours under reduced pressure to obtain the desired compound 0.68 g.

FAB MASS; 338 (M+1)
$^1$H-NMR (ppm, in CDCl$_3$); 0.97 (3H, t), 1.77 (2H, m), 3.93 (2H, q), 4.22 (4H, m), 6.63 (3H, m), 6.81 (1H, d, J=8.2 Hz), 7.24 (1H, dd, J=8.5, 2.1 Hz), 7.42 (1H, d, J=2.1 Hz), 7.57 (1H, d, J=8.5 Hz)

EXAMPLE 61
Synthesis of 2-[(1,4-benzodioxane)-6-methylene]-6-butoxy-3(2H)-benzofuranone After 2-[(1,4-benzodioxane)-6-methylene]-6-hydroxy-3(2H)-benzofuranone 1.0 g and potassium carbonate 1.95 g were added to dimethylformamide 10 ml, butyl iodide 0.70 ml was added, and the mixture was reacted at a temperature of 100° C. for two hours. After the solution was cooled to room temperature, ethyl acetate 200 ml was added, and the mixture was washed with water 50 ml twice and a saturated salt solution 50 ml twice. The ethyl acetate solution was dehydrated with anhydrous magnesium sulfate, and concentrated to 40 ml at a temperature of 40° C. under reduced pressure. The precipitated crystals were filtered and dried over phosphorous pentoxide at a temperature of 60° C. for four hours under reduced pressure to obtain the desired compound 0.74 g.

FAB MASS; 352 (M+1)
$^1$H-NMR (ppm, in CDCl$_3$); 0.97 (3H, t), 1.48 (2H, m), 1.77 (2H, m), 4.03 (2H, q), 4.28 (4H, m), 6.68–6.71 (3H, m), 6.87 (1H, d, J=8.2 Hz), 7.30 (1H, dd, J=8.5, 2.1 Hz), 7.48 (1H, d, J=1.8 Hz), 7.63 (1H, d, J=8.2 Hz)

EXAMPLE 62
Synthesis of 2-[(1,4-benzodioxane)-6-methylene]-6-pentyloxy-3(2H)-benzofuranone After 2-[(1,4-benzodioxane)-6-methylene]-6-hydroxy-3(2H)-benzofuranone 1.0 g and potassium carbonate 1.95 g were added to dimethylformamide 10 ml, n-pentyl iodide 0.79 ml was added, and the mixture was reacted at a temperature of 100° C. for two hours. After the solution was cooled to room temperature, ethyl acetate 200 ml was added, and the mixture was washed with water 100 ml three times and a saturated sodium chloride solution 50 ml twice. The ethyl acetate solution was dehydrated with anhydrous magnesium sulfate, and concentrated to 20 ml at a temperature of 40° C. under reduced pressure. The precipitated crystals were filtered and dried over phosphorous pentoxide at a temperature of 60° C. for four hours under reduced pressure to obtain the desired compound 0.95 g.

FAB MASS; 366 (M+1)
$^1$H-NMR (ppm, in CDCl$_3$); 0.92 (3H, t), 1.40 (4H, m), 1.80 (2H, m), 4.03 (2H, q), 4.28 (4H, m), 6.68–6.71 (3H, m), 6.88 (1H, d, J=8.5 Hz), 7.31 (1H, dd, J=8.5, 2.1 Hz), 7.49 (1H, d, J=2.1 Hz), 7.63 (1H, d, J=8.2 Hz)

EXAMPLE 63
Synthesis of 6-ethoxy-2-piperonylidene-3(2H)-benzofuranone

After 6-hydroxy-2-piperonylidene-3(2H)-benzofuranone 1 g and potassium carbonate 1.95 g were added to dimethylformamide 10 ml, ethyl iodide 0.48 ml was added, and the mixture was reacted at a temperature of 100° C. for two hours. After the solution was cooled to room temperature, ethyl acetate 200 ml was added. The ethyl acetate solution was washed with water 100 ml twice and a saturated sodium chloride solution 50 ml twice. The ethyl acetate solution was dehydrated with anhydrous magnesium sulfate, and concentrated to 40 ml under reduced pressure. The precipitated crystals were filtered and dried over phosphorous pentoxide at a temperature of 60° C. for four hours under reduced pressure to obtain the desired compound 0.65 g. FAB MASS; 311 (M+1) $^1$H-NMR (ppm, in CDCl$_3$); 1.45 (3H, t), 4.10 (2H, q), 6.00 (2H, s), 6.68–6.70 (3H, m), 6.82 (1H, d, J=7.9 Hz), 7.24 (1H, dd, J=8.2 Hz), 7.49 (1H, d, J=1.5 Hz), 7.63 (1H, d, J=8.2 Hz)

EXAMPLE 64
Synthesis of 6-propyloxy-2-piperonylidene-3(2H)-benzofuranone

After 6-hydroxy-2-piperonylidene-3(2H)-benzofuranone 1 g and potassium carbonate 1.95 g were added to dimethylformamide 10 ml, propyl iodide 0.59 ml was added, and the mixture was reacted at a temperature of 100° C. for two hours. After the solution was cooled to room temperature, ethyl acetate 200 ml was added. The ethyl acetate solution was washed with water 100 ml twice and a saturated sodium chloride solution 50 ml twice. The ethyl acetate solution was dehydrated with anhydrous magnesium sulfate, and concentrated to 40 ml under reduced pressure. The precipitated crystals were filtered and dried over phosphorous pentoxide at a temperature of 60° C. for four hours under reduced pressure to obtain the desired compound 0.61 g.

FAB MASS; 325 (M+1)
$^1$H-NMR (ppm, in CDCl$_3$); 1.04 (3H, t), 1.82 (2H, m), 3.99 (2H, q), 6.00 (2H, s), 6.70 (3H, m), 6.83 (1H, d, J=7.9 Hz), 7.24 (1H, d, J=7.6 Hz), 7.51 (1H, s), 7.64 (1H, d, J=9.1 Hz)

EXAMPLE 65
Synthesis of 6-butoxy-2-piperonylidene-3(2H)-benzofuranone

After 6-hydroxy-2-piperonylidene-3(2H)-benzofuranone 1 g and potassium carbonate 1.95 g were added to dimethylformamide 10 ml, butane 1-iodide 0.70 ml was added, and the mixture was reacted at a temperature of 100° C. for two hours. After the solution was cooled to room temperature, ethyl acetate 200 ml was added. The ethyl acetate solution was washed with water 100 ml twice and a saturated sodium chloride solution 50 ml twice. The ethyl acetate solution was dehydrated with anhydrous magnesium sulfate, and concentrated to 10 ml under reduced pressure. The precipitated crystals were filtered and dried over phosphorous pentoxide at a temperature of 60° C. for four hours under reduced pressure to obtain the desired compound 0.84 g.

FAB MASS; 339 (M+1)
$^1$H-NMR (ppm, in CDCl$_3$); 0.97 (3H, t), 1.48 (2H, m), 1.78 (2H, m), 4.03 (2H, q), 5.99 (2H, s), 6.68–6.70 (3H, m), 6.82 (1H, d, J=8.2 Hz), 7.24 (1H, dd, J=7.9, 1.5 Hz), 7.51 (1H, d, J=1.5 Hz), 7.63 (1H, d, J=8.8 Hz)

EXAMPLE 66
Synthesis of 6-pentyloxy-2-piperonylidene-3(2H)-benzofuranone

After 6-hydroxy-2-piperonylidene-3(2H)-benzofuranone 1 g and potassium carbonate 1.95 g were added to dimethylformamide 10 ml, n-pentyl iodide 0.79 ml was added, and the mixture was reacted at a temperature of 100° C. for two hours. After the solution was cooled to room temperature, ethyl acetate 200 ml was added. The ethyl acetate solution was washed with water 100 ml twice and a saturated sodium chloride solution 50 ml twice. The ethyl acetate solution was dehydrated with anhydrous magnesium sulfate, and concentrated to 15 ml under reduced pressure. The precipitated crystals were filtered and dried over phosphorous pentoxide at a temperature of 60° C. for four hours under reduced pressure to obtain the desired compound 0.97 g.

FAB MASS; 353 (M+1)
$^1$H-NMR (ppm, in CDCl$_3$); 0.93 (3H, t), 1.43 (4H, m), 1.82 (2H, m), 4.03 (2H, q), 6.00 (2H, s), 6.69–6.71 (3H, m), 6.83 (1H, d, J=8.2 Hz), 7.25 (1H, dd, J=7.9, 1.8 Hz), 7.51 (1H, d, J=1.8 Hz), 7.63 (1H, d, J=8.8 Hz)

EXAMPLE 67
Synthesis of 2-[(1,4-benzodioxane)-6-methylene]-6-hexyloxy-3(2H)-benzofuranone After 2-[(1,4-benzodioxane)-6-methylene]-6-hydroxy-3(2H)-benzofuranone 1 g and potassium carbonate 1.95 g were added to dimethylformamide 10 ml, n-hexyl iodide 0.89 ml was added, and the mixture was reacted at a temperature of 100° C. for two hours. After the solution was cooled to room temperature, ethyl acetate 200 ml was added. The ethyl acetate solution was washed with water 100 ml three times and a saturated sodium chloride solution 50 ml twice. The ethyl acetate solution was dehydrated with anhydrous magnesium sulfate, and concentrated to 20 ml under reduced pressure at a temperature of 40° C., and hexane 100 ml was added. The precipitated crystals were filtered and dried over phosphorous pentoxide at a temperature of 60° C. for four hours under reduced pressure to obtain the desired compound 0.83 g.

FAB MASS; 381 (M+1)
$^1$H-NMR (ppm, in CDCl$_3$); 0.89 (3H, t), 1.33 (4H, m), 1.44 (2H, m), 1.78 (2H, m), 4.01 (2H, q), 4.27 (4H, m), 6.68–6.70 (3H, m), 6.87 (1H, d, J=8.5 Hz), 7.31 (1H, dd, J=8.5, 1.8 Hz), 7.48 (1H, d, J=1.8 Hz), 7.63 (1H, d, J=8.8 Hz)

EXAMPLE 68
Synthesis of 6-hexyloxy-2-piperonylidene-3(2H)-benzofuranone

After 6-hydroxy-2-piperonylidene-3(2H)-benzofuranone 1 g and potassium carbonate 1.95 g were added to dimethylformamide 10 ml, n-hexyl iodide 0.89 ml was added, and the mixture was reacted at a temperature of 100° C. for two hours. After the solution was cooled to room temperature, ethyl acetate 200 ml was added. The ethyl acetate solution was washed with water 100 ml twice and a saturated sodium chloride solution 50 ml twice. The ethyl acetate solution was dehydrated with anhydrous magnesium sulfate, and concentrated to 40 ml under reduced pressure, and hexane 100 ml was added. The precipitated crystals were filtered and dried over phosphorous pentoxide at a temperature of 60° C. for four hours under reduced pressure to obtain the desired compound 0.82 g.

FAB MASS; 367 (M+1)
$^1$H-NMR (ppm, in CDCl$_3$); 0.89 (3H, t), 1.33 (4H, m), 1.44 (2H, m), 1.80 (2H, m), 4.04 (2H, q), 6.01 (2H, s), 6.69–6.71 (3H, m), 6.84 (1H, d, J=7.9 Hz), 7.26 (1H, dd, J=8.2, 1.5 Hz), 7.52 (1H, d, J=1.5 Hz), 7.63 (1H, d, J=7.6 Hz)

EXAMPLE 69
Synthesis of methyl-2-({2-[1-(2,3-dihydro-1,4-benzodioxine-6-yl)methylidene]-3-oxo-2,3-dihydrobenzo[b]furan-6-yl}oxy)propionate After 2-[(1,4-benzodioxane)-6-methylene]-6-hydroxy-3(2H)-benzofuranone 1.0 g and potassium carbonate 1.16 g were added to dimethylformamide 10 ml, methyl 2-bromopropionate 0.67 g was added, and the mixture was reacted at a temperature of 110° C. for 16 hours. After the solution was cooled to room temperature, ethyl acetate 150 ml was added. The ethyl acetate solution was washed with water 150 ml twice and a saturated sodium chloride solution 100 ml. The ethyl acetate solution was dehydrated with anhydrous magnesium sulfate, and concentrated at a temperature of 40° C. under reduced pressure to obtain the concentrated oil. The residue was fractionated by silica gel column chromatography (silica gel: 100 g, eluted with solvent of hexane:ethyl acetate=1:1) to obtain the desired material as oil. The residue was dissolved in ethyl acetate 20 ml, the precipitated crystals were filtered, and the desired compound 0.421 g was obtained.

FAB MASS; 383 (M+1)
$^1$H-NMR (ppm, in CDCl$_3$); 1.65 (3H, d), 3.78 (3H, s), 4.28 (4H, m), 4.84 (1H, m), 6.64 (1H, d, J=1.8 Hz), 6.70 (1H, s), 6.72 (1H, dd, J=8.5, 2.1 Hz), 6.88 (1H, d, J=8.5 Hz), 7.30 (1H, dd, J=8.2, 1.8 Hz), 7.48 (1H, d, J=1.8 Hz), 7.66 (1H, d, J=8.5 Hz)

EXAMPLE 70
Synthesis of 2-({2-[1-(2,3-dihydro-1,4-benzodioxine-6-yl)methylidene]-3-oxo-2,3-dihydrobenzo[b]furan-6-yl}oxy)propionic acid After methyl 2-({2-[1-(2,3-dihydro-1,4-benzodioxine-6-yl)methylidene]-3-oxo-2,3-dihydrobenzo[b]furan-6-yl}oxy)propionate 100 mg was dissolved in a mixed solution of methanol 10 ml and 1,4-dioxane 15 ml, 4 N-sodium hydroxide 10 ml was added, and the mixture was stirred at room temperature for one hour. The reaction solution was adjusted to pH 4 with 2N-hydrochloric acid, and extracted with ethyl acetate 150 ml to obtain the desired material. The ethyl acetate solution was washed with water 100 ml twice and a saturated sodium chloride solution 10 ml twice, dehydrated with anhydrous magnesium sulfate, and concentrated to 20 ml at a temperature of 40° C. under reduced pressure. The precipitated crystals were filtered and dried at a temperature of 60° C. under reduced pressure to obtain the desired compound 47.7 mg.

FAB MASS; 369 (M+1)
$^1$H-NMR (ppm, in DMSO-d$_6$); 1.55 (3H, d), 4.28 (4H, m), 5.13 (1H, m), 6.75 (1H, s), 6.80 (1H, dd, J=8.5, 2.1 Hz), 6.95 (1H, d, J=8.5 Hz), 7.04 (1H, d, J=1.8 Hz), 7.44 (1H, dd, J=8.2, 1.8 Hz), 7.51 (1H, d, J=2.1 Hz), 7.65 (1H, d, J=8.8 Hz)

EXAMPLE 71
Synthesis of methyl-2-methoxy-4-[(3-oxo-2.3-dihvdrobenzo[b]furan-2-ylidene)methyl]benzoate 2H-benzofuran-3-one 1 g and vanillin acetate 2.17 g were dissolved in dichloromethane 25 ml, aluminum oxide (manufactured by Merck Co., cat. No. 1076) 24.3 g was added, and the mixture was stirred for 1.5 hours, and aluminum oxide was filtered to obtain a reaction solution. Aluminum oxide was washed with dichloromethane 100 ml three times. This solution and the reaction solution were combined and concentrated at a temperature of 40° C. under reduced pressure. The concentrate was dissolved in methanol 40 ml, the solution was allowed to stand at room temperature for two hours. The precipitated crystals were filtered, and the resulting crystals were dried at a temperature of 60° C. for two hours under reduced pressure to obtain the desired compound 1.44 g.

FAB MASS; 311 (M+1)

$^1$H-NMR (ppm, in CDCl$_3$); 2.28 (3H, s), 3.87 (3H, s), 6.94(1H, s), 7.22 (1H, d, J=8.2 Hz), 7.32 (1H, t, J=7.6 Hz), 7.54 (1H, m), 7.64 (1H, dd, J=8.2, 1.5 Hz), 7.21 (1H, d, J=1.8 Hz), 7.78–7.81 (3H, m)

EXAMPLE 72

Synthesis of 2-methoxy-4-[(3-oxo-2,3-dihydrobenzo [b]furan-2-ylidene)methyl]benzoate After methyl 2-methoxy-4-[3-oxo-2,3-dihydrobenzo[b] furan-2 -ylidene)methyl]benzoate 0.6 g was dissolved in a mixed solution of methanol 5 ml and 1,4-dioxane 10 ml, 4N sodium hydroxide 2 ml was added, and the mixture was stirred for five hours. The reaction solution was adjusted to pH 2 with 2N-hydrochloric acid, and the precipitated crystals were filtered. The resulting crystals were dried at a temperature of 60° C. for four hours under reduced pressure to obtain the desired compound 0.45 g. FAB MASS; 297 (M+1)

$^1$H-NMR (ppm, in DMSO-d$_6$); 3.87 (3H, s), 6.87 (1H, s), 6.92 (1H, d, J=8.2 Hz), 7.29 (1H, t, J=7.3 Hz), 7.51 (2H, m), 7.58 (1H, d, J=1.8 Hz), 7.74–7.77 (2H, m)

EXAMPLE 73

Synthesis of 2-[1-(1H-5-indolyl)methylidene]-2,3-dihydrobenzo[b]furan-3-one 2H-benzofuran-3-one 1 g and 4-formylindol 1.29 g were dissolved in dichloromethane 25 ml, aluminum oxide (manufactured by Merck Co., cat. No. 1076) 24.0 g was added, and the mixture was stirred for two hours, and aluminum oxide was filtered to obtain a reaction solution. Aluminum oxide was washed with dichloromethane 150 ml twice. The dichloromethane solution and the reaction solution were combined and concentrated at a temperature of 40° C. under reduced pressure. The concentrate was dissolved in methanol 20 ml, the solution was allowed to stand at room temperature for two hours. The precipitated crystals were filtered, and the resulting crystals were dried at a temperature of 60° C. for two hours under reduced pressure to obtain the desired compound 1.22 g.

FAB MASS; 262 (M+1)

$^1$H-NMR (ppm, in DMSO-d$_6$); 6.56 (1H, d, J=3.0 Hz), 7.08 (1H, s), 7.30 (1H, t, 25 J=7.3 Hz), 7.44 (1H, d, J=3.0 Hz), 7.52 (1H, d, J=8.5 Hz), 7.58 (1H, m), 7.76–7.83 (3H, m), 8.25 (1H, d, J=1.5 Hz)

TEST EXAMPLE 1

In vitro 17β-HSD inhibition activity test

17β-HSD inhibition activity of the compounds obtained in Examples 1– 73 (abbreviated as a test material hereinafter) was tested. Namely, each test material was dissolved in ethanol to obtain a solution of 260 nM of final concentration, placed in a test tube, and evaporated to dryness in nitrogen gas. To the material, a buffer solution of 10 mM phosphate 590 μg (pH 7.5) containing 100 mM potassium chloride, 1 mM ethylenediamine tetraacetic acid, 0.5 mM nicotinamide adenine dinucleotidephosphate of a reducing type (all chemicals were available from Wako Junyaku Company) and 1 μM [4-$^{14}$C]estrone (NEN Research Products Company), and a microsome fraction 10 μl obtained from human placenta according to a method of E. A. Thompson et al (J. Biol. Chem., vol. 249, 5364–5372 (1974)) were added, and the mixture was reacted with shaking for 30 minutes at a temperature of 37° C. After the reaction, dichloromethane 2 ml was added at once. The mixture was thoroughly stirred, and centrifuged for five minutes at 3,000 rpm. The resulting lower layer (a dichloromethane layer) was removed to another test tube, and evaporated to dryness. To the tube, ethanol 100 μl containing estrone 20 μg and estradiol 20 μg was added, and 20 μl of the mixture was spotted on a TLC plate (silica gel 60 F$_{254}$, Merck Company). After the TLC plate was developed with benzene:acetone (4:1), spots corresponding to estrone and estradiol were cut off under ultraviolet light, liquid scintillation cocktail (Filter count (trademark); Hewlett Packard Company) was added to determine the amount of residual [4-$^{14}$C] estrone, and the amount of [4-$^{14}$C] estradiol produced by 17 μ-HSD enzyme activity by using a liquid scintillation counter. Further, as a control group, similar operation is conducted without adding the test materials. The 17β-HSD enzyme activity of the control group was determined as 0% of inhibition ratio, and the 17β-HSD enzyme inhibition ratio of the test materials were determined by percentage. The results are shown in FIGS. 1–8.

TEST EXAMPLE 2

An in vivo test for determining the amount of serum estradiol

Using young female rats, which were treated with gonadotropic hormone, the amount of serum estradiol was determined. Namely, SD type female rats of 14 days were previously bred along with their nursing parents and weaned at 20 days, and at 21 days, pregnant mare's serum gonadotropin of 600 IU per kg of weight dissolved in physiological saline was administered by subcutaneous injection. After 24 hours, a test material suspended in 0.5% carboxymethyl cellulose, which was dissolved in physiological saline of 100 mg per kg of weight, was orally administered. After 4 and 24 hours, whole blood was collected from the caudal vena cava under ether anesthesia, and the serum was separated by centrifugation for 30 minutes at 3,000 rpm. The amount of estradiol in the serum of rats, which had been administered the test material, was determined by using a E2 kit "Daiichi" II (Daiichi Radioisotope Kenkyusho Co.). Each 100 μl of the serum of rats and estradiol having known concentration for a standard curve was added into each test tube, diethyl ether of 3 ml was added, and the mixture was well-stirred and allowed to stand a minute. When the ether layer and water layer were clearly separated, the bottom of the tube was immersed in dry ice-methanol to freeze only the water layer, and the ether layer was removed in other test tube and evaporated to dryness at a temperature of 37° C. in nitrogen gas. Into this tube, 100 μgI $^{125}$I-estradiol and anti-estradiol antibody, which were contained in the kit, were added, and the mixture was reacted at room temperature for 90 minutes. After finishing the reaction, secondary antibody 1 ml was added, and the mixture was reacted further for 15 minutes and centrifuged at 3,000 rpm for 15 minutes. The supernatant was thoroughly removed with an aspirator, and $^{125}$I-estradiol in the residue was determined with a gamma-counter. A standard curve was drawn from the amount of $^{125}$I-estradiol by known concentration of estradiol, and the amount of estradiol contained in the serum of the rats administered the test material was calculated. The results are shown in FIGS. 1–8.

Industrial Applicability method for producing the derivatives can be provided. The derivatives of the present invention have inhibition activity of 17β-HSD, and for the activity, these derivatives are useful for a therapeutic agent for preventing and/or treating androgen or estrogen dependent diseases, particularly, prostatic cancer, benign prostatic hyperplasia, virilism, mammary cancer, mastopathy, endometrical cancer, endometriosis, ovarian cancer and the like.

What is claimed is:

1. A new benzofuranone derivative represented by the following general formula (I):

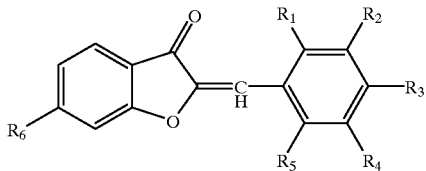

wherein $R_1$–$R_5$ represent hydrogen, a hydroxy group, or a straight or branched alkyl, alkyloxy or aralkyloxy group having 1–7 carbon atoms, a halogen, an amino group or an alkylene dioxy group joined at $R_1$ and $R_2$, $R_2$ and $R_3$, $R_3$ and $R_4$, or $R_4$ and $R_5$, respectively, $R_6$ represents a hydroxy group, or a straight or branched alkyloxy or an aralkyloxy group having 1–7 carbon atoms, or a caroboxylic acid ester having 1–7 carbon atoms with the proviso that when $R_2$ and $R_6$ are both hydroxy, then $R_1$, $R_3$, $R_4$ and $R_5$ are not hydrogen and further when $R_6$ is a hydroxy group, and $R_1$ $R_2$, $R_4$ and $R_5$ are hydrogen, then $R_3$ is not a methoxy group and still further when $R_2$ and $R_6$ are both hydroxy, and $R_1$, $R_4$ and $R_5$ are hydrogen, then $R_3$ is not hydroxy and yet still further when $R_4$ and $R_6$ are both hydroxy, and $R_1$, $R_2$ and $R_5$ are hydrogen, then $R_3$ is not hydroxy.

2. A method for producing the new benzofuranone derivative claimed in claim 1, characterized in that it comprises dissolving a benzofuranone compound represented by the following general formula (II) and a benzaldehyde compound represented by the following general formula (III) in an organic solvent, refluxing with heating or reacting at room temperature, under acidic or basic conditions, and purifying the desired compound from the reactant:

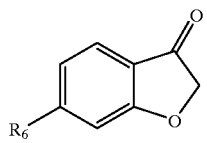

wherein $R_6$ represents a hydroxy group, a straight or branched alkyloxy or aralkyloxy group having 1–7 carbon atoms, or a carboxylic acid ester having 1–7 carbon atoms:

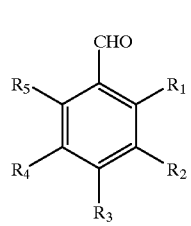

wherein $R_1$–$R_5$ represent hydrogen, a hydroxy group, or a straight or branched alkyl, alkyloxy or aralkyloxy group having 1–7 carbon atoms, a halogen, or an amino group, respectively.

3. A medicine comprising the new benzofuranone derivative claimed in claim 1 as an effective ingredient.

4. A therapeutic agent for hormone dependent diseases comprising the new benzofuranone derivative claimed in claim 1 as an effective ingredient.

5. The compound according to claim 1, wherein said benzofuranone derivative is a member selected from the group consisting of
2-[(3-chloro-6-aminophenyl)methylene]-6-hydroxy-3(2H)-benzofuranone;
2-[(4-chloro-3-aminophenyl)methylene]-6-hydroxy-3(2H)-benzofuranone;
2-[(4,6-dimethoxyphenyl)methylene]-6-hydroxy-3(2H)-benzofuranone;
2-[(3,5-dimethoxyphenyl)methylene]-6-hydroxy-3(2H)-benzofuranone;
2-[(2,5-dimethoxyphenyl)methylene]-6-hydroxy-3(2H)-benzofuranone;
2-[(1,4-benzodioxane)-6-methylene]-6-hydroxy-3(2H)-benzofuranone;
2-[(indol)-3-methylene]-6-hydroxy-3(2H)-benzofuranone;
2-[(4-isopropylphenyl)methylene]-6-hydroxy-3(2H)-benzofuranone;
2-[(3,4-diethoxyphenyl)methylene]-6-hydroxy-3(2H)-benzofuranone;
2-[(3-methoxy-4-ethoxyphenyl)methylene]-6-hydroxy-3(2H)-benzofuranone;
2-[(3-methoxy-4-benzyloxyphenyl)methylene]-6-hydroxy-3(2H)-benzofuranone;
2-[(4-methoxy-3-benzyloxyphenyl)methylene]-6-hydroxy-3(2H)-benzofuranone;
2-[(3,4-dibenzyloxyphenyl)methylene]-6-hydroxy-3(2H)-benzofuranone;
2-[(3-ethoxy-4-hydroxyphenyl)methylene]-6-hydroxy-3(2H)-benzofuranone;
2-[(3-ethoxy-4-benzyloxyphenyl)methylene]-6-hydroxy-3(2H)-benzofuranone;
2-[(3-phenoxyphenyl)methylene]-6-hydroxy-3(2H)-benzofuranone;
2-[(3-methyl-4-methoxyphenyl)methylene]-6-hydroxy-3(2H)-benzofuranone;
[E]-2-[(3,4-dimethoxyphenyl)methylene]-6-hydroxy-3(2H)-benzofuranone;
2-[(3-ethoxy-4-methoxyphenyl)methylene]-6-hydroxy-3(2H)-benzofuranone;
2-[(3,4-dimethylphenyl)methylene]-6-hydroxy-3(2H)-benzofuranone;
2-[(3-methyl-4-hydoxyphenyl)methylene]-6-hydroxy-3(2H)-benzofuranone;
2-[(1,4-bezodioxane)-6-methylene]-6-acetoxy-3(2H)-benzofuranone;
6-acetoxy-2-piperonylidene-3(2H)-benzofuranone;
2-[(3-methoxyphenyl)methylene]-6-acetoxy-3(2H)-benzofuranone;
2-[(3,4-dimethoxyphenyl)methylene]-6-acetoxy-3(2H)-benzofuranone;
2-[(3,5-dimethoxyphenyl)methylene]-6-acetoxy-3(2H)-benzofuranone;
2-[(3-methyl-4-methoxyphenyl)methylene]-6-acetoxy-3(2H)-benzofuranone;
2-[(3,4-dimethoxyphenyl)methylene]-6-benzoyloxy-3(2H)-benzofuranone;
2-[(3,5-dimethoxyphenyl)methylene]-6-benzoyloxy-3(2H)-benzofuranone;
6-benzoyloxy-2-piperonylidene-3(2H)-benzofuranone;
2-[(1,4-benzodioxane)-6-methylene]-6-benzoyloxy-3(2H)-benzofuranone;
2-[(3-methyl-4-methoxyphenyl)methylene]-6-benzoyloxy-3(2H)-benzofuranone;

2-[(3-methoxyphenyl)methylene]-6-benzoyloxy-3(2H)-benzofuranone;
2-[(4-methoxyphenyl)methylene]-6-benzoyloxy-3(2H)-benzofuranone;
2-[(4-methoxyphenyl)methylene]-6-propionyloxy-3(2H)-benzofuranone;
2-[(3-methoxyphenyl)methylene]-6-propionyloxy-3(2H)-benzofuranone;
2-[(3-methyl-4-methoxyphenyl)methylene]-6-propionyloxy-3(2H)-benzofuranone;
2-[(3,5-dimethoxyphenyl)methylene]-6-propionyloxy-3(2H)-benzofuranone;
2-[(3,4-dimethoxyphenyl)methylene]-6-propionyloxy-3(2H)-benzofuranone;
6-propionyloxy-2-piperonylidene-3(2H)-benzofuranone;
2-[(1,4-benzodioxane)-6-methylene]-6-propionyloxy-3(2H)-benzofuranone;
2-[(4-methoxyphenyl)methylene]-6-isopropyloxy-3(2H)-benzofuranone;
2-[(3-methoxyphenyl)methylene]-6-isopropyloxy-3(2H)-benzofuranone;
2-[(3,4-dimethoxyphenyl)methylene]-6-isopropyloxy-3(2H)-benzofuranone;
2-[(3,5-dimethoxyphenyl)methylene]-6-isopropyloxy-3(2H)-benzofuranone;
2-[(3-methyl-4-methoxyphenyl)methylene]-6-isopropyloxy-3(2H)-benzofuranone;
2-[(1,4-benzodioxane)-6-methylene]-6-isopropyloxy-3(2H)-benzofuranone;
6-isopropyloxy-2-piperonylidene-3(2H)-benzofuranone;
2-[(3-methyl-4-methoxyphenyl)methylene]-6-methoxy-3(2H)-benzoftiranone;
2-[(1,4-benzodioxane)-6-methylene]-6-methoxy-3(2H)-benzofuranone;
2-[(3-methoxyphenyl)methylene]-6-methoxy-3(2H)-benzofuranone;
2-[(2,4-ditnethoxyphenyl)methylene]-6-hydroxy-3(2H)-benzofuranone;
2-[(3-methoxy-4-propyloxyphenyl)methylene]-6-hydroxy-3(2H)-benzofuranone;
2-[(3-methoxy-4-butoxyphenyl)methylene]-6-hydroxy-3(2H)-benzofuranone;
2-[(3-methoxy-4-pentyloxyphenyl)methylene]-6-hydroxy-3(2H)-benzofuranone;
2-[(3-methoxy-4-hexyloxyphenyl)methylene]-6-hydroxy-3(2H)-benzoftiranone;
2-[(1,4-benzodioxane)-6-methylene]-6-ethoxy-3(2H)-benzofuranone;
2-[(1,4-benzodioxane)-6-methylene]-6-propyloxy-3(2H)-benzofuranone;
2-[(1,4-benzodioxane)-6-methylene]-6-butoxy-3(2H)-benzofuranone;
2-[(1,4-benzodioxane)-6-methylene]-6-pentyloxy-3(2H)-benzofuranone;
6-ethoxy-2-piperonylidene-3(2H)-benzofuranone;
6-propyloxy-2-piperonylidene-3(2H)-benzofuranone;
6-butoxy-2-piperonylidene-3(2H)-benzofuranone;
6-pentyloxy-2-piperonylidene-3(2H)-benzofuranone;
2-[(1,4-benzodioxane)-6-methylene]-6-hexyloxy-3(2H)-benzofuranone;
6-hexyloxy-2-piperonylidene-3(2H)-benzofuranone
methyl-2-({2-[1-(2,3-dihydro-1,4-benzodioxine-6-yl)methylidene]-3-oxo-2,3-dihydrobenzo[b]furan-6-yl}oxy)propionate;
2-({2-[1-(2,3-dihydro-1,4-benzodioxine-6-yl)methylidene]-3-oxo-2,3-dihydrobenzo[b]furan-6-yl}oxy)propionic acid;
methyl-2-methoxy-4-[(3-oxo-2,3-dihydrobenzo[b]furan-2-ylidene)methyl]benzoate; and
2-methoxy-4-[(3-oxo-2,3-dihydrobenzo[b]furan-2-ylidene)methyl]benzoate.

6. A pharmaceutical composition comprising: a compound of the formula (I):

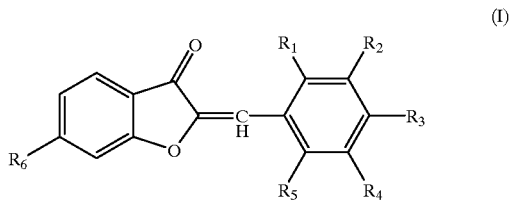

wherein $R_1$–$R_5$ represent hydrogen, a hydroxy group, or a straight or branched alkyl, alkyloxy or aralkyloxy group having 1–7 carbon atoms, a halogen, an amino group or an alkylene dioxy group joined at $R_1$ and $R_2$, $R_2$ and $R_3$, $R_3$ and $R_4$, or $R_4$ and $R_5$, respectively, $R_6$ represents a hydroxy group, or a straight or branched alkyloxy or an aralkyloxy group having 1–7 carbon atoms, or a caroboxylic acid ester having 1–7 carbon atoms with the proviso that when $R_2$ and R6 are both hydroxy, then $R_1$, $R_3$, $R_4$ and $R_5$ are not hydrogen and further when $R_6$ is a hydroxy group, and $R_1$ $R_2$, $R_4$ and $R_5$ are hydrogen, then $R_3$ is not a methoxy group and still further when $R_2$ and $R_6$ are both hydroxy, and $R_1$, $R_4$ and $R_5$ are hydrogen then $R_3$ is not hydroxy and yet still further when $R_4$ and $R_6$ are both hydroxy, and $R_1$, $R_2$ and $R_5$ are hydrogen, then $R_3$is not hydroxy;
and a pharmaceutically acceptable carrier.

7. The pharmaceutical composition according to claim 6, wherein said compound is a member selected from the group consisting of
2-[(3-chloro-6-aminophenyl)methylene]-6-hydroxy-3(2H)-benzofuranone;
2-[(4-chloro-3-aminophenyl)methylene]-6-hydroxy-3(2H)-benzofuranone;
2-[(4,6-dimethoxyphenyl)methylene]-6-hydroxy-3(2H)-benzofuranone;
2-[(3,5-dimethoxyphenyl)methylene]-6-hydroxy-3(2H)-benzofuranone;
2-[(2,5-dimethoxyphenyl)methylene]-6-hydroxy-3(2H)-benzofuranone;
2-[(1,4-benzodioxane)-6-methylene]-6-hydroxy-3(2H)-benzofuranone;
2-[(indol)-3-methylene]-6-hydroxy-3(2H)-benzofuranone;
2-[(4-isopropylphenyl)methylene]-6-hydroxy-3(2H)-benzofuranone;
2-[(3,4-diethoxyphenyl)methylene]-6-hydroxy-3(2H)-benzofuranone;
2-[(3-methoxy-4-ethoxyphenyl)methylene]-6-hydroxy-3(2H)-benzofuranone;
2-[(3-methoxy-4-benzyloxyphenyl)methylene]-6-hydroxy-3(2H)-benzofuranone;
2-[(4-methoxy-3-benzyloxyphenyl)methylene]-6-hydroxy-3(2H)-benzofuranone;
2-[(3,4-dibenzyloxyphenyl)methylene]-6-hydroxy-3(2H)-benzofuranone;
2-[(3-ethoxy-4-hydroxyphenyl)methylene]-6-hydroxy-3(2H)-benzofuranone;
2-[(3-ethoxy-4-benzyloxyphenyl)methylene]-6-hydroxy-3(2H)-benzofuranone;
2-[(3-phenoxyphenyl)methylene]-6-hydroxy-3(2H)-benzofuranone;

2-[(3-methyl-4-methoxyphenyl)methylene]-6-hydroxy-3(2H)-benzofuranone;
[E]-2-[(3,4-dimethoxyphenyl)methylene]-6-hydroxy-3(2H)-benzofuranone;
2-[(3-ethoxy-4-methoxyphenyl)methylene]-6-hydroxy-3(2H)-benzofuranone;
2-[(3,4-dimethylphenyl)methylene]-6-hydroxy-3(2H)-benzofuranone;
2-[(3-methyl-4-hydoxyphenyl)methylene]-6-hydroxy-3(2H)-benzofuranone;
2-[(1,4-bezodioxane)-6-methylene]-6-acetoxy-3(2H)-benzofuranone;
6-acetoxy-2-piperonylidene-3(2H)-benzofuranone;
2-[(3-methoxyphenyl)methylene]-6-acetoxy-3(2H)-benzofuranone;
2-[(3,4-dimethoxyphenyl)methylene]-6-acetoxy-3(2H)-benzofuranone;
2-[(3,5-dimethoxyphenyl)methylene]-6-acetoxy-3(2H)-benzofuranone;
2-[(3-methyl-4-methoxyphenyl)methylene]-6-acetoxy-3(2H)-benzofuranone;
2-[(3,4-dimethoxyphenyl)methylene]-6-benzoyloxy-3(2H)-benzofuranone;
2-[(3,5-dimethoxyphenyl)methylene]-6-benzoyloxy-3(2H)-benzofuranone;
6-benzoyloxy-2-piperonylidene-3(2H)-benzofuranone;
2-[(1,4-benzodioxane)-6-methylene]-6-benzoyloxy-3(2H)-benzofuranone;
2-[(3-methyl-4-methoxyphenyl)methylene]-6-benzoyloxy-3(2H)-benzofuranone;
2-[(3-methoxyphenyl)methylene]-6-benzoyloxy-3(2H)-benzofuranone;
2-[(4-methoxyphenyl)methylene]-6-benzoyloxy-3(2H)-benzofuranone;
2-[(4-methoxyphenyl)methylene]-6-propionyloxy-3(2H)-benzofuranone;
2-[(3-methoxyphenyl)methylene]-6-propionyloxy-3(2H)-benzofuranone;
2-[(3-methyl-4-methoxyphenyl)methylene]-6-propionyloxy-3(2H)-benzofuranone;
2-[(3,5-dimethoxyphenyl)methylene]-6-propionyloxy-3(2H)-benzofuranone;
2-[(3,4-dimethoxyphenyl)methylene]-6-propionyloxy-3(2H)-benzofuranone;
6-propionyloxy-2-piperonylidene-3(2H)-benzofuranone;
2-[(1,4-benzodioxane)-6-methylene]-6-propionyloxy-3(2H)-benzofuranone;
2-[(4-methoxyphenyl)methylene]-6-isopropyloxy-3(2H)-benzofuranone;
2-[(3-methoxyphenyl)methylene]-6-isopropyloxy-3(2H)-benzofuranone;
2-[(3,4-dimethoxyphenyl)methylene]-6-isopropyloxy-3(2H)-benzofuranone;
2-[(3,5-dimethoxyphenyl)methylene]-6-isopropyloxy-3(2H)-benzofuranone;
2-[(3-methyl-4-methoxyphenyl)methylene]-6-isopropyloxy-3(2H)-benzofuranone;
2-[(1,4-benzodioxane)-6-methylene]-6-isopropyloxy-3(2H)-benzofuranone;
6-isopropyloxy-2-piperonylidene-3(2H)-benzofuranone;
2-[(3-methyl-4-methoxyphenyl)methylene]-6-methoxy-3(2H)-benzofuranone;
2-[(1,4-benzodioxane)-6-methylene]-6-methoxy-3(2H)-benzofuranone;
2-[(3-methoxyphenyl)methylene]-6-methoxy-3(2H)-benzofuranone;
2-[(2,4-dimethoxyphenyl)methylene]-6-hydroxy-3(2H)-benzofuranone;
2-[(3-methoxy-4-propyloxyphenyl)methylene]-6-hydroxy-3(2H)-benzofuranone;
2-[(3-methoxy-4-butoxyphenyl)methylene]-6-hydroxy-3(2H)-benzofuranone;
2-[(3-methoxy-4-pentyloxyphenyl)methylene]-6-hydroxy-3(2H)-benzofuranone;
2-[(3-methoxy-4-hexyloxyphenyl)methylene]-6-hydroxy-3(2H)-benzofuranone;.
2-[(1,4-benzodioxane)-6-methylene]-6-ethoxy-3(2H)-benzofuranone;
2-[(1,4-benzodioxane)-6-methylene]-6-propyloxy-3(2H)-benzofuranone;
2-[(1,4-benzodioxane)-6-methylene]-6-butoxy-3(2H)-benzofuranone;
2-[(1,4-benzodioxane)-6-methylene]-6-pentyloxy-3(2H)-benzofuranone;
6-ethoxy-2-piperonylidene-3(2H)-benzofuranone;
6-propyloxy-2-piperonylidene-3(2H)-benzofuranone;
6-butoxy-2-piperonylidene-3(2H)-benzofuranone;
6-pentyloxy-2-piperonylidene-3(2H)-benzofuranone;
2-[(1,4-benzodioxane)-6-methylene]-6-hexyloxy-3(2H)-benzofuranone;
6-hexyloxy-2-piperonylidene-3(2H)-benzofuranone
methyl-2-({2-[1-(2,3-dihydro-1,4-benzodioxine-6-yl)methylidene]-3-oxo-2,3-dihydrobenzo[b]furan-6-yl}oxy)propionate;
2-({2-[1-(2,3-dihydro-1,4-benzodioxine-6-yl)methylidene]-3-oxo-2,3-dihydrobenzo[b]furan-6-yl}oxy)propionic acid;
methyl-2-methoxy-4-[(3-oxo-2,3-dihydrobenzo[b]furan-2-ylidene)methyl]benzoate; and
2-methoxy-4-[(3-oxo-2,3-dihydrobenzo[b]furan-2-ylidene)methyl]benzoate.

8. A method for treating an androgen or estrogen dependent disease in a mammal, said method comprising: administering a compound of the formula (I):

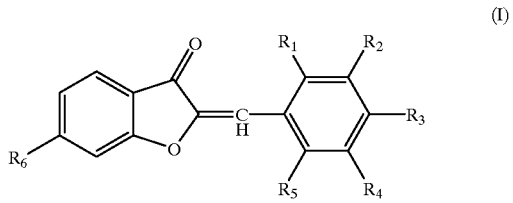

wherein $R_1$–$R_5$ represent hydrogen, a hydroxy group, or a straight or branched alkyl, alkyloxy or aralkyloxy group having 1–7 carbon atoms, a halogen, an amino group or an alkylene dioxy group joined at $R_1$ and $R_2$, $R_2$ and $R_3$, $R_3$ and $R_4$, or $R_4$ and $R_5$, respectively, $R_6$ represents a hydroxy group, or a straight or branched alkyloxy or an aralkyloxy group having 1–7 carbon atoms, or a caroboxylic acid ester having 1–7 carbon atoms.

9. The method according to claim 8, wherein said compound is a member selected from the group consisting of
2-[(3-hydroxyphenyl)methylene]-6-hydroxy-3(2H)-benzofuranone;
2-[(3-chloro-6-aminophenyl)methylene]-6-hydroxy-3(2H)-benzofuranone;
2-[(4-chloro-3-aminophenyl)methylene]-6-hydroxy-3(2H)-benzofuranone;
2-[(4,6-dimethoxyphenyl)methylene]-6-hydroxy-3(2H)-benzofuranone;
2-[(3,5-dimethoxyphenyl)methylene]-6-hydroxy-3(2H)-benzofuranone;

2-[(2,5-dimethoxyphenyl)methylene]-6-hydroxy-3(2H)-benzofuranone;
2-[(1,4-benzodioxane)-6-methylene]-6-hydroxy-3(2H)-benzofuranone;
2-[(indol)-3-methylene]-6-hydroxy-3(2H)-benzofuranone;
2-[(4-isopropylphenyl)methylene]-6-hydroxy-3(2H)-benzofuranone; and
2-[(3-methoxyphenyl)methylene]-6-hydroxy-3(2H)-benzofuranone;
2-[(3,4-diethoxyphenyl)methylene]-6-hydroxy-3(2H)-benzofuranone;
2-[(3-methoxy-4-ethoxyphenyl)methylene]-6-hydroxy-3(2H)-benzofuranone;
2-[(3-methoxy-4-benzyloxyphenyl)methylene]-6-hydroxy-3(2H)-benzofuranone;
2-[(4-methoxy-3-benzyloxyphenyl)methylene]-6-hydroxy-3(2H)-benzofuranone;
2-[(3,4-dibenzyloxyphenyl)methylene]-6-hydroxy-3(2H)-benzofuranone;
2-[(3-ethoxy-4-hydroxyphenyl)methylene]-6-hydroxy-3(2H)-benzofuranone;
2-[(3-ethoxy-4-benzyloxyphenyl)methylene]-6-hydroxy-3(2H)-benzofuranone;
2-[(3-phenoxyphenyl)methylene]-6-hydroxy-3(2H)-benzofuranone;
2-[(3-methyl-4-methoxyphenyl)methylene]-6-hydroxy-3(2H)-benzofuranone;
[E]-2-[(3,4-dimethoxyphenyl)methylene]-6-hydroxy-3(2H)-benzofuranone;
2-[(3-ethoxy-4-methoxyphenyl)methylene]-6-hydroxy-3(2H)-benzofuranone;
2-[(3,4-dimethylphenyl)methylene]-6-hydroxy-3(2H)-benzofuranone;
2-[(3-methyl-4-hydoxyphenyl)methylene]-6-hydroxy-3(2H)-benzofuranone;
2-[(1,4-bezodioxane)-6-methylene]-6-acetoxy-3(2H)-benzofuranone;
6-acetoxy-2-piperonylidene-3(2H)-benzofuranone;
2-[(3-methoxyphenyl)methylene]-6-acetoxy-3(2H)-benzofuranone;
2-[(3,4-dimethoxyphenyl)methylene]-6-acetoxy-3(2H)-benzofuranone;
2-[(3,5-dimethoxyphenyl)methylene]-6-acetoxy-3(2H)-benzofuranone;
2-[(3-methyl-4-methoxyphenyl)methylene]-6-acetoxy-3(2H)-benzofuranone;
2-[(3,4-dimethoxyphenyl)methylene]-6-benzoyloxy-3(2H)-benzofuranone;
2-[(3,5-dimethoxyphenyl)methylene]-6-benzoyloxy-3(2H)-benzofuranone;
6-benzoyloxy-2-piperonylidene-3(2H)-benzofuranone;
2-[(1,4-benzodioxane)-6-methylene]-6-benzoyloxy-3(2H)-benzofuranone;
2-[(3-methyl-4-methoxyphenyl)methylene]-6-benzoyloxy-3(2H)-benzofuranone;
2-[(3-methoxyphenyl)methylene]-6-benzoyloxy-3(2H)-benzofuranone;
2-[(4-methoxyphenyl)methylene]-6-benzoyloxy-3(2H)-benzofuranone;
2-[(4-methoxyphenyl)methylene]-6-propionyloxy-3(2H)-benzofuranone;
2-[(3-methoxyphenyl)methylene]-6-propionyloxy-3(2H)-benzofuranone;
2-[(3-methyl-4-methoxyphenyl)methylene]-6-propionyloxy-3(2H)-benzofuranone;
2-[(3,5-dimethoxyphenyl)methylene]-6-propionyloxy-3(2H)-benzofuranone;
2-[(3,4-dimethoxyphenyl)methylene]-6-propionyloxy-3(2H)-benzofuranone;
6-propionyloxy-2-piperonylidene-3(2H)-benzofuranone;
2-[(1,4-benzodioxane)-6-methylene]-6-propionyloxy-3(2H)-benzofuranone;
2-[(4-methoxyphenyl)methylene]-6-isopropyloxy-3(2H)-benzofuranone;
2-[(3-methoxyphenyl)methylene]-6-isopropyloxy-3(2H)-benzofuranone;
2-[(3,4-dimethoxyphenyl)methylene]-6-isopropyloxy-3(2H)-benzofuranone;
2-[(3,5-dimethoxyphenyl)methylene]-6-isopropyloxy-3(2H)-benzofuranone;
2-[(3-methyl-4-methoxyphenyl)methylene]-6-isopropyloxy-3(2H)-benzofuranone;
2-[(1,4-benzodioxane)-6-methylene]-6-isopropyloxy-3(2H)-benzofuranone;
6-isopropyloxy-2-piperonylidene-3(2H)-benzofuranone;
2-[(3-methyl-4-methoxyphenyl)methylene]-6-methoxy-3(2H)-benzofuranone;
2-[(1,4-benzodioxane)-6-methylene]-6-methoxy-3(2H)-benzofuranone;
2-[(3-methoxyphenyl)methylene]-6-methoxy-3(2H)-benzofuranone;
2-[(2,4-dimethoxyphenyl)methylene]-6-hydroxy-3(2H)-benzofuranone;
2-[(3-methoxy-4-propyloxyphenyl)methylene]-6-hydroxy-3(2H)-benzofuranone;
2-[(3-methoxy-4-butoxyphenyl)methylene]-6-hydroxy-3(2H)-benzofuranone;
2-[(3-methoxy-4-pentyloxyphenyl)methylene]-6-hydroxy-3(2H)-benzofuranone;
2-[(3-methoxy-4-hexyloxyphenyl)methylene]-6-hydroxy-3(2H)-benzofuranone;
2-[(1,4-benzodioxane)-6-methylene]-6-ethoxy-3(2H)-benzofuranone;
2-[(1,4-benzodioxane)-6-methylene]-6-propyloxy-3(2H)-benzofuranone;
2-[(1,4-benzodioxane)-6-methylene]-6-butoxy-3(2H)-benzofuranone;
2-[(1,4-benzodioxane)-6-methylene]-6-pentyloxy-3(2H)-benzofuranone;
6-ethoxy-2-piperonylidene-3(2H)-benzofuranone;
6-propyloxy-2-piperonylidene-3(2H)-benzofuranone;
6-butoxy-2-piperonylidene-3(2H)-benzofuranone;
6-pentyloxy-2-piperonylidene-3(2H)-benzofuranone;
2-[(1,4-benzodioxane)-6-methylene]-6-hexyloxy-3(2H)-benzofuranone;
6-hexyloxy-2-piperonylidene-3(2H)-benzofuranone
methyl-2-({2-[1-(2,3-dihydro-1,4-benzodioxine-6-yl)methylidene]-3-oxo-2,3-dihydrobenzo[b]furan-6-yl}oxy)propionate;
2-({2-[1-(2,3-dihydro-1,4-benzodioxine-6-yl)methylidene]-3-oxo-2,3-dihydrobenzo[b]furan-6-yl}oxy)propionic acid;
methyl-2-methoxy-4-[(3-oxo-2,3-dihydrobenzo[b]furan-2-ylidene)methyl]benzoate; and
2-methoxy-4-[(3-oxo-2,3-dihydrobenzo[b]furan-2-ylidene)methyl]benzoate.

10. The method according to claim 8, wherein said disease is a 17β-hydroxysteroid dehydrogenase mediated disease.

* * * * *